US008278368B2

(12) United States Patent
Rusin et al.

(10) Patent No.: US 8,278,368 B2
(45) Date of Patent: Oct. 2, 2012

(54) DENTAL FILLERS, METHODS, COMPOSITIONS INCLUDING A CASEINATE

(75) Inventors: Richard P. Rusin, Woodbury, MN (US); Sumita B. Mitra, West St. Paul, MN (US); Kevin M. Cummings, Little Canada, MN (US); Paul A. Burgio, St. Paul, MN (US); Afshin Falsafi, Woodbury, MN (US)

(73) Assignee: 3M Innnovatve Properties Company, St. Pauk, MN (US)

( * ) Notice: Subject to any disclaimer, the term of this patent is extended or adjusted under 35 U.S.C. 154(b) by 798 days.

(21) Appl. No.: 11/719,472

(22) PCT Filed: Nov. 7, 2005

(86) PCT No.: PCT/US2005/040340
§ 371 (c)(1),
(2), (4) Date: May 6, 2009

(87) PCT Pub. No.: WO2006/055328
PCT Pub. Date: May 26, 2006

(65) Prior Publication Data
US 2009/0304809 A1     Dec. 10, 2009

(51) Int. Cl.
*A61K 6/083* (2006.01)
*C08K 9/06* (2006.01)
*A61C 5/00* (2006.01)
*B32B 19/00* (2006.01)

(52) U.S. Cl. ......... 523/116; 523/118; 523/214; 524/25; 524/26; 433/216; 433/217.1; 433/228.1; 424/52; 424/57; 428/357

(58) Field of Classification Search ................. 523/116, 523/118, 214; 524/25, 26; 433/216, 217, 433/228.1, 217.1; 424/52, 57; 428/357
See application file for complete search history.

(56) References Cited

U.S. PATENT DOCUMENTS

| | | | |
|---|---|---|---|
| 2,323,550 A * | 7/1943 | Lukens | 524/425 |
| 3,786,116 A | 1/1974 | Milkovich et al. | |
| 3,804,794 A * | 4/1974 | Schmitt et al. | 523/116 |
| 3,842,059 A | 10/1974 | Milkovich et al. | |
| 3,926,870 A | 12/1975 | Keegan et al. | |
| 4,141,864 A | 2/1979 | Rijke et al. | |
| 4,259,075 A | 3/1981 | Yamauchi et al. | |
| 4,298,738 A | 11/1981 | Lechtken et al. | |
| 4,324,744 A | 4/1982 | Lechtken et al. | |
| 4,356,296 A | 10/1982 | Griffith et al. | |
| 4,385,109 A | 5/1983 | Lechtken et al. | |
| 4,499,251 A | 2/1985 | Omura et al. | |
| 4,503,169 A | 3/1985 | Randklev | |
| 4,518,430 A | 5/1985 | Brown et al. | |
| 4,537,940 A | 8/1985 | Omura et al. | |
| 4,539,382 A | 9/1985 | Omura et al. | |
| 4,612,053 A | 9/1986 | Brown et al. | |
| 4,642,126 A | 2/1987 | Zador et al. | |
| 4,648,843 A | 3/1987 | Mitra | |
| 4,652,274 A | 3/1987 | Boettcher et al. | |
| 4,684,673 A | 8/1987 | Adachi | |
| 4,695,251 A | 9/1987 | Randklev | |
| 4,698,318 A | 10/1987 | Vogel et al. | |
| 4,710,523 A | 12/1987 | Lechtken et al. | |
| 4,737,593 A | 4/1988 | Ellrich et al. | |
| 4,871,786 A | 10/1989 | Aasen et al. | |
| 4,872,936 A | 10/1989 | Engelbrecht | |
| 4,880,660 A | 11/1989 | Aasen et al. | |
| 5,015,628 A | 5/1991 | Reynolds | |
| 5,037,639 A | 8/1991 | Tung | |
| 5,055,497 A | 10/1991 | Okada et al. | |
| 5,074,916 A | 12/1991 | Hench et al. | |
| 5,076,844 A | 12/1991 | Fock et al. | |
| 5,130,347 A | 7/1992 | Mitra | |
| 5,135,396 A | 8/1992 | Kuboki | |
| 5,154,762 A | 10/1992 | Mitra et al. | |
| 5,162,267 A | 11/1992 | Smyth | |
| 5,192,815 A | 3/1993 | Okada et al. | |
| 5,296,026 A | 3/1994 | Monroe et al. | |
| 5,332,429 A | 7/1994 | Mitra et al. | |
| 5,340,776 A | 8/1994 | Paschke et al. | |
| 5,468,477 A | 11/1995 | Kumar et al. | |
| 5,501,727 A | 3/1996 | Wang et al. | |
| 5,508,342 A | 4/1996 | Antonucci et al. | |
| 5,525,648 A | 6/1996 | Aasen et al. | |
| 5,530,038 A | 6/1996 | Yamamoto et al. | |
| 5,545,676 A | 8/1996 | Palazzotto et al. | |
| 5,571,502 A | 11/1996 | Winston et al. | |

(Continued)

FOREIGN PATENT DOCUMENTS
EP     0 173 567 A2    3/1986
(Continued)

OTHER PUBLICATIONS

ANSI/ADA Spec. No. 27 "Resin-Based Filling Materials," pp. 1-27 (1993).
ASTM D 2805-95, "Standard Test Method for Hiding Power of Paints by Reflectometry," pp. 115-119, 1995.
Data Sheet: Comparison of RECALDENT (PP-ACP) Technology, GC America Inc. 1 pg, 2006.
Hench et al., "Bioactive Glasses," in Introduction to Bioceramics, L.L. Hench & J. Wilson, Eds., World Scientific Publishing (1993), Chapter 3, pp. 41-61.
Höland et al., "Machineable and Phosphate Glass-Ceramics," in Introduction to Bioceramics, L.L. Hench & J. Wilson, Eds., World Scientific Publishing (1993), Chapter 8, pp. 125-136.
IUPAC Nomenclature of Inorganic Chemistry, Recommendations 1990.
Kawakami et al., "Silicone Macromers for Graft Polymer Synthesis", Polymer J. 14, 913-917(1982).
Kawakami et al., "Synthesis and Copolymerization of Polysiloxane Macromers", ACS Polymer Preprints 25 (1), 245-246 (1984).

(Continued)

*Primary Examiner* — Tae H Yoon
(74) *Attorney, Agent, or Firm* — Julie A. Lapos-Kuchar; Sean J. Edman

(57) ABSTRACT

The present application provides dental fillers, and methods of making and using dental fillers that include a treated surface that includes a caseinate. Dental compositions including such dental fillers can be useful for delivering ions to the oral environment. Dental compositions, and methods of using dental compositions that include a caseinate and a hardenable resin or a water-dispersible, polymeric film former are also provided.

57 Claims, No Drawings

U.S. PATENT DOCUMENTS

| | | | |
|---|---|---|---|
| 5,603,922 A | 2/1997 | Winston et al. |
| 5,607,663 A | 3/1997 | Rozzi et al. |
| 5,614,175 A | 3/1997 | Winston et al. |
| 5,641,347 A | 6/1997 | Grabowski et al. |
| 5,662,887 A | 9/1997 | Rozzi et al. |
| 5,693,313 A | 12/1997 | Shiraishi et al. |
| 5,725,882 A | 3/1998 | Kumar et al. |
| 5,735,942 A | 4/1998 | Litkowski et al. |
| 5,762,950 A | 6/1998 | Yli-Urpo et al. |
| 5,833,957 A | 11/1998 | Winston et al. |
| 5,866,630 A | 2/1999 | Mitra et al. |
| 5,876,208 A | 3/1999 | Mitra et al. |
| 5,883,153 A | 3/1999 | Roberts et al. |
| 5,888,491 A | 3/1999 | Mitra et al. |
| 5,891,233 A | 4/1999 | Salonen et al. |
| 5,891,448 A | 4/1999 | Chow et al. |
| 5,910,273 A | 6/1999 | Thiel et al. |
| 5,922,786 A | 7/1999 | Mitra et al. |
| 5,958,915 A | 9/1999 | Abe et al. |
| 5,980,697 A | 11/1999 | Kolb et al. |
| 5,981,475 A | 11/1999 | Reynolds |
| 6,030,606 A | 2/2000 | Holmes |
| 6,036,494 A | 3/2000 | Cohen |
| 6,036,944 A | 3/2000 | Winston et al. |
| 6,063,832 A | 5/2000 | Yuhda et al. |
| 6,086,374 A | 7/2000 | Litkowski et al. |
| 6,136,737 A | 10/2000 | Todo et al. |
| 6,136,885 A | 10/2000 | Rusin et al. |
| 6,180,688 B1 | 1/2001 | Rheinberger et al. |
| 6,244,871 B1 | 6/2001 | Litkowski et al. |
| 6,251,963 B1 | 6/2001 | Köhler et al. |
| 6,270,562 B1 | 8/2001 | Jia |
| 6,297,181 B1 | 10/2001 | Kunert et al. |
| 6,306,926 B1 | 10/2001 | Bretscher et al. |
| 6,312,668 B2 | 11/2001 | Mitra et al. |
| 6,338,751 B1 | 1/2002 | Litkowski et al. |
| 6,353,039 B1 | 3/2002 | Rheinberger et al. |
| 6,355,704 B1 | 3/2002 | Nakatsuka et al. |
| 6,372,198 B1 | 4/2002 | Abbate |
| 6,387,981 B1 | 5/2002 | Zhang et al. |
| 6,398,859 B1 | 6/2002 | Dickens et al. |
| 6,413,538 B1 | 7/2002 | Garcia et al. |
| 6,426,114 B1 | 7/2002 | Troczynski et al. |
| 6,437,019 B1 | 8/2002 | Rusin et al. |
| 6,451,290 B2 | 9/2002 | Winston et al. |
| 6,458,868 B1 | 10/2002 | Okada et al. |
| 6,461,632 B1 | 10/2002 | Gogolewski |
| 6,521,264 B1 | 2/2003 | Lacout et al. |
| 6,572,693 B1 | 6/2003 | Wu et al. |
| 6,596,061 B1 | 7/2003 | Rentschler |
| 6,613,812 B2 | 9/2003 | Bui et al. |
| 6,632,412 B2 | 10/2003 | Peltola et al. |
| 6,649,669 B2 | 11/2003 | Dickens |
| 6,652,875 B1 | 11/2003 | Bannister |
| 6,709,744 B1 | 3/2004 | Day et al. |
| 6,730,156 B1 | 5/2004 | Windisch et al. |
| 6,733,818 B2 | 5/2004 | Luo et al. |
| 6,750,268 B2 | 6/2004 | Hino |
| 6,765,036 B2 | 7/2004 | Dede et al. |
| 6,770,265 B2 | 8/2004 | Ishihara et al. |
| 6,770,325 B2 | 8/2004 | Troczynski et al. |
| 6,780,844 B1 | 8/2004 | Reynolds |
| 6,790,877 B2 | 9/2004 | Nakatsuka et al. |
| 6,818,682 B2 | 11/2004 | Falsafi et al. |
| 6,923,989 B2 | 8/2005 | Lacout et al. |
| 6,960,079 B2 | 11/2005 | Brennan et al. |
| 6,982,288 B2 | 1/2006 | Mitra et al. |
| 7,090,720 B2 | 8/2006 | Kessler et al. |
| 7,090,721 B2 | 8/2006 | Craig et al. |
| 7,156,911 B2 | 1/2007 | Kangas et al. |
| 7,173,074 B2 | 2/2007 | Mitra et al. |
| 7,255,562 B2 | 8/2007 | Rusin et al. |
| 2003/0082232 A1 | 5/2003 | Lee et al. |
| 2003/0157357 A1 | 8/2003 | Rusin et al. |
| 2003/0158302 A1 | 8/2003 | Chaput et al. |
| 2003/0167967 A1 | 9/2003 | Narhi et al. |
| 2003/0181541 A1 | 9/2003 | Wu et al. |
| 2004/0052860 A1 | 3/2004 | Reid et al. |
| 2004/0185013 A1 | 9/2004 | Burgio et al. |
| 2004/0206932 A1 | 10/2004 | Abuelyaman |
| 2004/0241238 A1 | 12/2004 | Sepulveda et al. |
| 2005/0175965 A1 | 8/2005 | Craig et al. |
| 2005/0175966 A1 | 8/2005 | Falsafi et al. |
| 2005/0176844 A1 | 8/2005 | Aasen et al. |
| 2005/0201987 A1 | 9/2005 | Pirhonen et al. |
| 2005/0256223 A1 | 11/2005 | Kolb et al. |

FOREIGN PATENT DOCUMENTS

| | | |
|---|---|---|
| EP | 0 201 031 A2 | 11/1986 |
| EP | 0 201 778 A1 | 11/1986 |
| EP | 0 201 778 B1 | 12/1988 |
| EP | 0 201 031 B1 | 8/1989 |
| EP | 0 344 832 A1 | 12/1989 |
| EP | 0 373 384 A1 | 6/1990 |
| EP | 0 344 832 B1 | 10/1992 |
| EP | 0 373 384 B1 | 10/1992 |
| EP | 0 634 373 A1 | 1/1995 |
| EP | 0 712 622 A1 | 5/1996 |
| EP | 0 712 622 B1 | 9/1999 |
| EP | 1 051 961 A1 | 11/2000 |
| EP | 1 285 646 A1 | 2/2003 |
| EP | 1 051 961 B1 | 2/2006 |
| GB | 1 434 081 | 4/1976 |
| GB | 1 560 992 | 2/1980 |
| JP | 4-198112 | 7/1992 |
| JP | 4-329960 | 11/1992 |
| JP | 6-321515 | 11/1994 |
| JP | 9703843 | 4/1998 |
| JP | 10167942 | 6/1998 |
| SU | 1 792 695 | 2/1993 |
| WO | WO 87/07615 | 12/1987 |
| WO | WO 93/12760 A1 | 7/1993 |
| WO | WO 95/22956 A1 | 8/1995 |
| WO | WO 97/36943 | 10/1997 |
| WO | WO 98/17236 | 4/1998 |
| WO | WO 99/07326 A2 | 2/1999 |
| WO | WO 99/07326 A3 | 2/1999 |
| WO | WO 99/34772 A1 | 7/1999 |
| WO | WO 00/06108 A1 | 2/2000 |
| WO | WO 00/38619 A2 | 7/2000 |
| WO | WO 00/40206 A1 | 7/2000 |
| WO | WO 00/42092 A1 | 7/2000 |
| WO | WO 01/07444 A1 | 2/2001 |
| WO | WO 01/30305 A1 | 5/2001 |
| WO | WO 01/30306 A1 | 5/2001 |
| WO | WO 01/30307 A1 | 5/2001 |
| WO | WO 01/41822 A1 | 6/2001 |
| WO | WO 01/92271 A1 | 12/2001 |
| WO | WO 02/49578 | 6/2002 |
| WO | WO 02/072038 A1 | 9/2002 |
| WO | WO 02/085313 A1 | 10/2002 |
| WO | WO 02/094204 A1 | 11/2002 |
| WO | WO 03/052164 A2 | 6/2003 |
| WO | WO 03/063804 A1 | 8/2003 |
| WO | WO 03/074009 A1 | 9/2003 |
| WO | WO 04/000252 A1 | 12/2003 |
| WO | WO 2004/035029 A1 | 4/2004 |
| WO | WO 2004/035077 A1 | 4/2004 |
| WO | WO 2004/060327 A1 | 7/2004 |
| WO | WO 2005/018581 | 3/2005 |
| WO | WO 2006/020760 A1 | 2/2006 |
| WO | WO 2006/055317 A1 | 5/2006 |
| WO | WO 2006/055327 A1 | 5/2006 |
| WO | WO 2006/055329 A2 | 5/2006 |

OTHER PUBLICATIONS

Kawakami et al., "Synthesis of Silicone Graft Polymers and a Study of Their Surface Active Properties", Makromol. Chem. 185, 9-18 (1984).

Kokubo et al., "A/W Glass Ceramics: Processing and Properties," in Introduction to Bioceramics, L.L. Hench & J. Wilson, Eds., World Scientific Publishing, Chapter 5, pp. 75-88, (1993).

Mazzaoui, et al. "Incorporation of Casein Phosphopeptide-Amorphous Calcium Phosphate into a Glass-ionomer Cement" Journal of Dental Research, vol. 82, No. 11, Nov. 2003, pp. 914-918.

McKenzie, Advances in Protein Chemistry, 22:75-135 (1967).

NSI Dental Pty Ltd., Hornsby Australia, Product Labeling, Dentacal Mouth Moistener [Undated], 1 page.

NSI Dental Pty Ltd., Hornsby Australia, Topacal, C-5 Product Information and Supporting Publications, V4, May 2003.

NSI Dental Pty Ltd., Hornsby Australia, Topical C-5, Enamel Improving Cream, Product Packaging [Undated], 1 page.

Product Advertisement, Recaldent, Victoria Australia, found in Journal of Dental Research, V. 84, No. 1, Jan. 2005, 1 page.

Product data sheet (i.e. sales or company literature): "AMCO—Casehesive™ Protein Polymers" datasheet. American Casein Company, Burlington, New Jersey, Oct. 3, 2001, 1 pg.

Product data sheet (i.e. sales or company literature): "AMCO—Edible Powdered Protein Products (p. 2)" datasheet [online]. American Casein Company, Burlington, New Jersey, Sep. 6, 2004 [retrieved on Feb. 9, 2005]. Retrieved from the Internet<URL: http://www.americancasein.com/edible_2.htm>; 1 pg.

Product data sheet (i.e. sales or company literature): "AMCO—Protein Polymers for Technical Applications" (p. 1) datasheet [online]. American Casein Company, Burlington, New Jersey, Sep. 6, 2004 [retrieved on Feb. 9, 2005]. Retrieved from the Internet<URL: http://www.americancasein.com/technical.htm>; 1 pg.

Product data sheet (i.e. sales or company literature): "American Casein Company—AMCO" datasheet [online]. American Casein Company, Burlington, New Jersey, Sep. 6, 2004 [retrieved on Feb. 9, 2005]. Retrieved from the Internet<URL:http://www.americancasein.com>; 2pgs.

Product data sheet (i.e. sales or company literature): "Bone—replacement individually designed—3di Ltd." datasheet [online]. 3di Ltd., Saalbahnhofstr, Germany, no date available [retrieved on Feb. 9, 2005]. Retrieved from the Internet<URL:http://www.3di.de/_englisch/materialspezifika/material/htm>; 1 pg.

Product data sheet (i.e. sales or company literature): "Bone—replacement individually designed—3di Ltd." datasheet [online]. 3di Ltd., Saalbahnhofstr, Germany, no date available [retrieved on Feb. 9, 2005]. Retrieved from the Internet<URL: http://www.3di.de/_englisch/materialspezifika/biovert.htm>; 1 pg.

Product data sheet (i.e. sales or company literature): "Cerabone A-W Cerabone A-W Iliac Spacer", Nippon Electric Glass Co., Ltd, Shiga, Japan, [no print date available], 8 pages.

Product data sheet (i.e. sales or company literature): "Cerabone A-W Artificial Vertebrae, Intervertebral Spacer, Spinous Process Spacer," Nippon Electric Glass Co., Ltd, Shiga, Japan, [no print date available], 8 pages.

Product data sheet (i.e. sales or company literature): "Corporate Chronology Nippon Electric Glass 50 Years and Beyond" datasheet [online]. Nippon Electric Glass Co., Ltd., Otsu, Shiga, Japan, Aug. 1, 1998 [retrieved on Feb. 9, 2005]. Retrieved from the Internet<URL:http://www.neg.co.jp/eng/company/history.html>; 4 pgs.

Product data sheet (i.e. sales or company literature): "NSI Dental—Manufacturer of dental restoratives for the dental practitioner" datasheet [online]. NSI Dental Pty Limited, Hornsby, Australia, no date available [retrieved on Feb. 9, 2005]. Retrieved from the Internet:<URL:http://www.nsidental.com/>; 5 pgs.

Product data sheet (i.e. sales or company literature): "Revitalize Teeth! NovaMin Tooth Remineralization for Oral Care Products" datasheet [online]. NovaMin Technology Inc, Alachua, FL, no date available [retrieved on Feb. 9, 2005]. Retrieved from the Internet<URL: http://www.novamin.com/>; 1 pg.

Product data sheet (i.e. sales or company literature): "Welcome to Recaldent" datasheet [online]. Recaldent Pty Ltd, University of Melbourne, Australia, no date available [retrieved on Feb. 9, 2005]. Retrieved from the Internet<URL: http://www.recaldent.com/index.htm>; 1 pg.

Reynolds, et al. "Retention in Plaque and Remineralization of Enamel Lesions by Various Forms of Calcium in a Mouthrinse or Sugar-free Chewing Gum" Journal of Dental Research, vol. 82, No. 3, Mar. 2003, pp. 206-211.

Ribadeau Dumas et al. "Structure primaire de la caséine β bovine," Eur. J. Biochem., 25:505, pp. 505-514, (1972).

Shen, et al. "Remineralization of Enamel Subsurface Lesions by Sugar-free Chewing Gum Containing Casein Phosphopeptide-Amorphous Calcium Phosphate" Journal of Dental Research, vol. 80, No. 12, Dec. 2001, pp. 2066-2070.

Tantbirojin, "Surface Modulation of Dental Hard Tissues," Ph.D. Thesis, University of MN, pp. 217, (1998).

The Merck Index, An Encyclopedia of Chemical, Drugs, and Biologicals, Twelfth Edition, Merck & Co., Inc., Whitehouse Station, NJ, pp. 309-310(1996).

Yamamuro, "A/W Glass Ceramics: Clinical Applications," in Introduction to Bioceramics, L.L. Hench & J. Wilson, Eds., World Scientific Publishing, Chapter 6, pp. 89-103, (1993).

Ana et al. "Effects of added bioactive glass on the setting and mechanical properties of resin-modified glass ionomer cement" *Biomaterials*, Elsevier Science Publishers BV., Barking, GB, vol. 24, No. 18, Aug. 2003, pp. 3061-3067, ISSN: 0142-9612.

ASTM D 2805-95, "Standard Test Method for Hiding Power of Paints by Reflectometry," 1995, pp. 115-119.

Cao et al. "Bioactive Materials" *Ceramics International*, Elsevier, Amsterdam, NL, 1996; 22(6):493-507.

*CRC Handbook of Chemistry and Physics*, 51st Edition, The Chemical Rubber Co., Cleveland, OH, Title page, copyright page, and p. B-77 (1970).

Data Sheet: Comparison of RECALDENT (PP-ACP) Technology, GC America Inc., Dec. 2006, 1 pg,.

Hench et al., "Bioactive Glasses," *An Introduction to Bioceramics*, L.L. Hench & J. Wilson, Eds., World Scientific Publishing (1993), Chapter 3, pp. 41-61.

Höland et al., "Machineable and Phosphate Glass-Ceramics," *An Introduction to Bioceramics*, L.L. Hench & J. Wilson, Eds., World Scientific Publishing (1993), Chapter 8, pp. 125-136.

Kawakami et al., "Silicone Macromers for Graft Polymer Synthesis," *Polymer J.*,1982; 14:913-917.

Kawakami et al., "Synthesis and Copolymerization of Polysiloxane Macromers," ACS Polymer Preprints, 1984; 25(1), 245-246.

Kawakami et al., "Synthesis of Silicone Graft Polymers and a Study of Their Surface Active Properties," *Makromol. Chem.*, 1984; 185:9-18.

Kokubo et al., "A/W Glass Ceramics: Processing and Properties," *An Introduction to Bioceramics*, L.L. Hench & J. Wilson, Eds., World Scientific Publishing, Chapter 5, pp. 75-88, (1993).

Mazzaoui, et al. "Incorporation of Casein Phosphopeptide-Amorphous Calcium Phosphate into a Glass-ionomer Cement" *Journal of Dental Research*, Nov. 2003; 82(11):914-918.

NSI Dental Pty Ltd., Hornsby Australia, Product Labeling, Dentacal Mouth Moistener, 1 page, use by 2005 on label.

Product data sheet (i.e. sales or company literature): "American Casein Company—AMCO" datasheet [online]. American Casein Company, Burlington, New Jersey, Sep. 6, 2004 [retrieved on Feb. 9, 2005-02]. Retrieved from the Internet:<URL:http://www.americancasein.com>; 2pgs.

Product data sheet (i.e. sales or company literature): "Bone—replacement individually designed—3di Ltd." datasheet [online]. 3di Ltd., Saalbahnhofstr, Germany, [retrieved on Feb. 9, 2005]. Retrieved from the Internet:<URL:http://www.3di.de/_englisch/materialspezifika/material/htm>; 1 pg.

Product data sheet (i.e. sales or company literature): "Bone—replacement individually designed—3di Ltd." datasheet [online]. 3di Ltd., Saalbahnhofstr, Germany, [retrieved on Feb. 9, 2005]. Retrieved from the Internet:<URL: http://www.3di.de/_englisch/materialspezifika/biovert.htm>: 1 pg.

Product data sheet (i.e. sales or company literature): "Cerabone A-W Cerabone A-W Iliac Spacer", Nippon Electric Glass Co., Ltd, Shiga, Japan, 8 pages.

Product data sheet (i.e. sales or company literature): "Cerabone A-W Artificial Vertebrae, Intervertebral Spacer, Spinous Process Spacer," Nippon Electric Glass Co., Ltd, Shiga, Japan, 8 pages.

Product data sheet (i.e. sales or company literature): "NSI Dental—Manufacturer of dental restoratives for the dental practitioner" datasheet [online]. NSI Dental Pty Limited, Hornsby, Australia, [retrieved on Feb. 9, 2005]. Retrieved from the Internet:<URL:http://www.nsidental.com/>; 5 pgs.

Product data sheet (i.e. sales or company literature): "Revitalize Teeth! NovaMin Tooth Remineralization for Oral Care Products" datasheet [online]. NovaMin Technology Inc, Alachua, FL, [retrieved on Feb. 9, 20059]. Retrieved from the Internet<URL: http://www.novamin.com/>; 1 pg.

Product data sheet (i.e. sales or company literature): "Welcome to Recaldent" datasheet [online]. Recaldent Pty Ltd, University of Melbourne, Australia, [retrieved on Feb. 9, 2005]. Retrieved from the Internet<URL: http://www.recaldent.com/index.htm>; 1 pg.

Reynolds, et al. "Retention in Plaque and Remineralization of Enamel Lesions by Various Forms of Calcium in a Mouthrinse or Sugar-free Chewing Gum" *Journal of Dental Research*, Mar. 2003; 82(3):206-211.

Ribadeau Dumas et al. "Structure primaire de la caseinée β bovine," *Eur. J. Biochem.*, 1972; 25:505-514. English language abstract.

Shen, et al. "Remineralization of Enamel Subsurface Lesions by Sugar-free Chewing Gum Containing Casein Phosphopeptide-Amorphous Calcium Phosphate" *Journal of Dental Research*, Dec. 2001; 80(12):2066-2070.

Skrtic et al., "Amorphous Calcium Phosphate-Based Bioactive Polymeric Composites for Mineralized Tissue Regeneration," *Journal of Research of the National Institute of Standards and Technology*, May-Jun. 2003; 108:167-182.

Tantbirojn, "Surface Modulation of Dental Hard Tissues," Ph.D. Thesis, University of MN, 234 pgs, (1998).

*The Merck Index, An Encyclopedia of Chemical, Drugs, and Biologicals*, Twelfth Edition, Merck & Co., Inc., Whitehouse Station, NJ, pp. 309-310 (1996).

Yamamuro, "A/W Glass Ceramics: Clinical Applications," *An Introduction to Bioceramics*, L.L. Hench & J. Wilson, Eds., World Scientific Publishing, Chapter 6, pp. 89-103, (1993).

Yli-Urpo et al., "Release of silica, calcium, phosphorus, and fluoride from glass ionomer cement containing bioactive glass," *Journal of Biomaterials Applications*, Jul. 2004; 19(1):pp. 5-20.

Extended European Search Report, EP10175466.1, dated Feb. 28, 2011.

* cited by examiner

DENTAL FILLERS, METHODS, COMPOSITIONS INCLUDING A CASEINATE

CROSS REFERENCE TO RELATED APPLICATIONS

This application is a national stage filing under 35 U.S.C. §371 of PCT/US2005/040340, filed Nov. 7, 2005, which claims priority to U.S. application Ser. No. 10/989523, filed Nov. 16, 2007, now abandoned, the disclosure of which is incorporated by reference in its entirety herein.

BACKGROUND

Demineralization of dental structures is well known to lead to caries, decayed dentin, cementum, and/or enamel, conditions that typically require treatment with a dental restorative, for example. Although such conditions can usually be adequately treated using dental restoratives, restored dental structures oftentimes can be susceptible to further decay around the margins of the restoration.

The release of ions (e.g., calcium, and preferably calcium and phosphorus) into the oral environment is known to enhance the natural remineralizing capability of dental structures. It is believed that enhanced remineralization may be a useful supplement to, or even an alternative to, traditional dental restorative methods. However, known compositions that release calcium and phosphorus into the oral environment (e.g., calcium phosphate containing compositions) oftentimes lack desirable properties including, for example, sustained release capabilities.

Thus, new compositions capable of releasing ions (e.g., phosphorus and other ions) into the oral environment are needed.

SUMMARY OF THE INVENTION

In one aspect, the present invention provides a dental filler including a treated surface, and methods of making and using such a dental filler including a treated surface. The treated surface includes a caseinate, which preferably includes a salt of calcium, phosphate, fluoride, or combinations thereof. Dental compositions including such a dental filler, and methods of using such dental compositions are also provided.

In another aspect, the present invention provides a dental composition that includes a hardenable resin and/or a water-dispersible, polymeric film former; and a caseinate, wherein the caseinate is at least partially dissolved, suspended, or dispersed in the hardenable resin and/or water-dispersible, polymeric film former. Preferably, the caseinate includes a salt of calcium, phosphate, fluoride, or combinations thereof. Methods of using such dental compositions are also provided.

Dental fillers and compositions as disclosed herein preferably lead to enhanced remineralization of dental structures, which can offer potential benefits including, for example, the ability to remineralize enamel and/or dentin lesions; to occlude exposed dentin and/or cementum tubules which cause sensitivity; to recondition abraded and/or etched enamel surfaces; to reseal microleakage regions at interfaces; and to increase resistance of contacted and nearby tooth structures to acid attack.

DEFINITIONS

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, a "self-etching" composition refers to a composition that bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions or chemical reactions forming radicals effective to polymerize ethylenically unsaturated compounds) involving one or more compounds capable of hardening or curing.

As used herein, a "dental structure surface" refers to tooth structures (e.g., enamel, dentin, and cementum) and bone.

As used herein, "dental material" refers to a material that may be bonded to a dental structure surface and includes, for example, dental restoratives, orthodontic appliances, and/or orthodontic adhesives.

As used herein, "(meth)acryl" is a shorthand term referring to "acryl" and/or "methacryl." For example, a "(meth)acryloxy" group is a shorthand term referring to either an acryloxy group (i.e., $CH_2=CHC(O)O-$) and/or a methacryloxy group (i.e., $CH_2=C(CH_3)C(O)O-$).

As used herein, an "amorphous" material is one which does not give rise to a discernible x-ray powder diffraction pattern. An "at least partially crystalline" material is one which gives rise to a discernible x-ray powder diffraction pattern.

As used herein, "groups" of the periodic table refer to and include groups 1-18 as defined in IUPAC Nomenclature of Inorganic Chemistry, Recommendations 1990.

As used herein, "a" or "an" means "at least one" or "one or more" unless otherwise indicated.

DETAILED DESCRIPTION OF PREFERRED EMBODIMENTS

The present invention provides dental fillers and/or compositions that include a caseinate. In some embodiments, a dental filler is provided that includes a treated surface that includes a caseinate. In some embodiments, dental compositions are provided that include such dental fillers. In some embodiments, dental compositions are provided that include a caseinate and a hardenable resin and/or a water-dispersible, polymeric film former. Methods of making and using such dental fillers and/or compositions are also provided.

Caseinates

Casein is a mixture of related phosphoproteins occurring in milk and cheese. As used herein, "casein" is meant to include one or more of the major casein components, which can be distinguished by electrophoresis and are commonly designated as α-, β-, γ-, and κ-caseins, in order of decreasing mobility at pH 7. The complete amino acid sequence of bovine β-casein is known and contains 209 residues with an approximate molecular weight of 23,600. See, for example, Ribadeaudumas et al., *Eur. J. Biochem.*, 25:505 (1972) and McKenzie, *Advan. Protein Chem.*, 22:75-135 (1967).

Casein is amphoteric and forms salts with both acids and bases. When both the cation and anion of a species (e.g., calcium phosphate) form salts with casein, the product is typically referred to as a complex (e.g., a calcium phosphate complex of casein. As used herein, the term "caseinate" is used to refer to salts and/or complexes of a casein.

Typical caseinates include, for example, salts of monovalent metals (e.g., sodium and potassium), salts of divalent metals (e.g., magnesium, calcium, strontium, nickel, copper, and zinc), salts of trivalent metals (e.g., aluminum), ammonium salts, phosphate salts (e.g., phosphate and fluorophosphate), and combinations thereof. Typical caseinate complexes include, for example, calcium phosphate complexes (available under the trade designation PHOSCAL from NSI Dental Pty. Ltd., Hornsby, Australia), calcium fluorophosphate complexes, calcium fluoride complexes, and combinations thereof.

Caseinates are typically available as dry powders. Caseinates may be either soluble or insoluble in aqueous fluids.

Surface Treatment of Dental Fillers

Preferably, the dental fillers are surface treated by methods similar to those described, for example, in U.S. Pat. No. 5,332,429 (Mitra et al.). In brief, the dental fillers described herein can be surface treated by combining the filler with a liquid having dissolved, dispersed, or suspended therein, a caseinate as described herein. The liquid or additional liquids may optionally include additional surface treating agents (e.g., fluoride ion precursors, silanes, titanates, etc). Optionally the liquid includes water, and if an aqueous liquid is used, it can be acidic or basic. Once treated, at least a portion of the liquid can be removed from the surface treated dental filler using any convenient technique (e.g., spray drying, oven drying, gap drying, lyophilizing, and combinations thereof). See, for example, U.S. Pat. No. 5,980,697 (Kolb et al.) for a description of gap drying. In one embodiment, the treated fillers can be oven dried, typically at drying temperatures of about 30° to about 100° C., for example, overnight. The surface treated filler can be further heated as desired. The treated and dried dental filler can then be screened or lightly comminuted to break up agglomerates. The resulting surface treated dental filler can be incorporated, for example, into a dental paste.

Dental fillers suitable for surface treatment can be selected from one or more of a wide variety of materials suitable for incorporation in compositions used for dental applications, such as fillers currently used in dental restorative compositions, and the like. Preferably the dental filler includes porous particles and/or porous agglomerates of particles. Preferred dental fillers include nanoparticles and/or agglomerates of nanoparticles. Preferred classes of fillers include metal oxides, metal fluorides, metal oxyfluorides, and combinations thereof, wherein the metal can be a heavy or non-heavy metal.

In preferred embodiments, the dental filler is an oxide, a fluoride, or an oxyfluoride of an element selected from the group consisting of Groups 2-5 elements, Groups 12-15 elements, Lanthanide elements, and combinations thereof. More preferably, the element is selected from the group consisting of Ca, Sr, Ba, Y, La, Ce, Pr, Nd, Pm, Sm Eu, Gd, Tb, Dy, Ho, Er, Tm, Yb, Lu, Ti, Zr, Ta, Zn, B, Al, Si, Sn, P, and combinations thereof. The dental filler can be a glass, an amorphous material, or a crystalline material. Optionally, the dental filler can include a source of fluoride ions. Such dental fillers include, for example, fluoroaluminosilicate glasses.

The filler is preferably finely divided. The filler can have a unimodial or polymodial (e.g., bimodal) particle size distribution. Preferably, the maximum particle size (the largest dimension of a particle, typically, the diameter) of the filler is less than 20 micrometers, more preferably less than 10 micrometers, and most preferably less than 5 micrometers. Preferably, the average particle size of the filler is less than 2 micrometers, more preferably less than 0.1 micrometers, and most preferably less than 0.075 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) fillet is especially preferred in certain embodiments.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

Other suitable fillers are disclosed, for example, in U.S. Pat. No. 6,306,926 (Bretscher et al.), U.S. Pat. No. 6,387,981 (Zhang et al.), U.S. Pat. No. 6,572,693 (Wu et al.), and U.S. Pat. No. 6,730,156 (Windisch et al.), as well as International Publication Nos. WO 01/30307 (Zhang et al.) and WO 03/063804 (Wu et al.). Filler components described in these references include nanosized silica particles, nanosized metal oxide particles, and combinations thereof. Nanofillers are also described in U.S. patent application Ser. Nos. 10/847,781; 10/847,782; and 10/847,803; all three of which were filed on May 17, 2004.

The surface treated dental filler preferably includes at least 0.01%, more preferably at least 0.05%, and most preferably at least 0.1% by weight caseinate, based on the total dry weight of the dental filler (i.e., excluding the liquid used in the treatment). The surface treated dental filler preferably includes at most 50%, more preferably at most 30%, and most preferably at most 20% by weight caseinate, based on the total dry weight of the dental filler (i.e., excluding the liquid used in the treatment).

For some embodiments of the present invention that include surface treated dental filler (e.g., dental adhesive compositions), the compositions preferably include at least 1% by weight, more preferably at least 2% by weight, and most preferably at least 5% by weight surface treated dental filler, based on the total weight of the composition. For such embodiments, compositions of the present invention preferably include at most 40% by weight, more preferably at most 20% by weight, and most preferably at most 15% by weight surface treated dental filler, based on the total weight of the composition.

For other embodiments (e.g., wherein the composition is a dental restorative or an orthodontic adhesive), compositions of the present invention preferably include at least 40% by weight, more preferably at least 45% by weight, and most preferably at least 50% by weight surface treated dental filler, based on the total weight of the composition. For such embodiments, compositions of the present invention preferably include at most 90% by weight, more preferably at most 80% by weight, even more preferably at most 70% by weight, and most preferably at most 50% by weight surface treated dental filler, based on the total weight of the composition.

Optionally, the treated surface of the dental filler can further include a silane (e.g., as described, for example, in U.S. Pat. No. 5,332,429 (Mitra et al.)), an antibacterial agent (e.g., chlorhexidine; quaternary ammonium salts; metal containing compounds such as Ag, Sn, or Zn containing compounds; and combinations thereof), and/or a source of fluoride ions (e.g., fluoride salts, fluoride containing glasses, fluoride containing compounds, and combinations thereof).

Dental Compositions Including a Caseinate

In some embodiments, the present invention provides dental compositions that include a caseinate and a hardenable resin and/or a water-dispersible, polymeric film former. Such dental compositions can be prepared either directly (e.g., by combining the caseinate with the hardenable resin or the water-dispersible, polymeric film former) or indirectly (e.g., by generating the caseinate in the hardenable resin or a water-dispersible, polymeric film former in situ). Suitable in situ methods of generating the caseinate include, for example, neutralization reactions, complexation reactions, and/or ion exchange reactions.

Dental compositions that include a caseinate in a hardenable resin include, for example, dental adhesives, dental restoratives, and orthodontic adhesives. Dental compositions that include a caseinate in a water-dispersible, polymeric film former include, for example, coatings, varnishes, sealants, primers, and desensitizers. In some embodiments as described herein above, the caseinate is present in a surface treated filler. In other embodiments, the caseinate is not present in a surface treated filler.

For embodiments in which a dental composition includes a caseinate in a hardenable resin, wherein the caseinate is not present in a surface treated filler, the dental composition preferably includes at least 0.01%, more preferably at least 0.1%, and most preferably at least 1% by weight caseinate, based on the total weight of the dental composition. For such embodiments, the dental composition preferably includes at most 70%, more preferably at most 50%, and most preferably at most 25% by weight caseinate, based on the total weight of the dental composition.

For embodiments in which a dental composition includes a caseinate in a water-dispersible, polymeric film former, wherein the caseinate is not present in a surface treated filler, the dental composition preferably includes at least 0.01%, more preferably at least 0.1%, and most preferably at least 1% by weight caseinate, based on the total weight of the dental composition. For such embodiments, the dental composition preferably includes at most 70%, more preferably at most 50%, and most preferably at most 25% by weight caseinate, based on the total weight of the dental composition.

Dental compositions of the present invention can also include optional additives as described herein below.

Dental compositions as described herein can be useful as dental primers, dental adhesives, cavity liners, cavity cleansing agents, cements, coatings, varnishes, orthodontic adhesives, restoratives, sealants, desensitizers, and combinations thereof.

Dental Compositions Including Hardenable Resins

Dental compositions of the present invention are useful for treating hard surfaces, preferably, hard tissues such as dentin, enamel, and bone. Such dental compositions can be aqueous or non-aqueous. In some embodiments, the compositions can be hardened (e.g., polymerized by conventional photopolymerization and/or chemical polymerization techniques) prior to applying the dental material. In other embodiments, the compositions can be hardened (e.g., polymerized by conventional photopolymerization and/or chemical polymerization techniques) after applying the dental material.

Suitable photopolymerizable compositions that can be used as dental materials and dental adhesive compositions in methods of the present invention can include epoxy resins (which contain cationically active epoxy groups), vinyl ether resins (which contain cationically active vinyl ether groups), ethylenically unsaturated compounds (which contain free radically active unsaturated groups, e.g., acrylates and methacrylates), and combinations thereof. Also suitable are polymerizable materials that contain both a cationically active functional group and a free radically active functional group in a single compound. Examples include epoxy-functional (meth)acrylates.

Ethylenically Unsaturated Compounds with Acid Functionality

As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates.

Ethylenically unsaturated compounds with acid functionality include, for example, α,β-unsaturated acidic compounds such as glycerol phosphate mono(meth)acrylates, glycerol phosphate di(meth)acrylates, hydroxyethyl (meth) acrylate (e.g., HEMA) phosphates, bis((meth)acryloxyethyl) phosphate, ((meth)acryloxypropyl) phosphate, bis((meth) acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis ((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth) acrylic acid, poly(meth)acrylated polycarboxylpolyphosphonic acid, poly(meth)acrylated polychlorophosphoric acid, poly(meth)acrylated polysulfonate, poly(meth)acrylated polyboric acid, and the like, may be used as components in the hardenable resin system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA: IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Provisional Application Ser. No. 60/600,658, filed on Aug. 11, 2004.

Preferably, the compositions of the present invention include at least 1% by weight, more preferably at least 3% by weight, and most preferably at least 5% by weight ethylenically unsaturated compounds with acid functionality, based on the total weight of the unfilled composition. Preferably, compositions of the present invention include at most 80% by weight, more preferably at most 70% by weight, and most preferably at most 60% by weight ethylenically unsaturated compounds with acid functionality, based on the total weight of the unfilled composition.

Ethylenically Unsaturated Compounds without Acid Functionality

The compositions of the present invention may also include one or more polymerizable components in addition to the ethylenically unsaturated compounds with acid functionality, thereby forming hardenable compositions. The polymerizable components may be monomers, oligomers, or polymers.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Preferably, compositions of the present invention include at least 5% by weight, more preferably at least 10% by weight, and most preferably at least 15% by weight ethylenically unsaturated compounds without acid functionality, based on the total weight of the unfilled composition. Preferably, compositions of the present invention include at most 95% by weight, more preferably at most 90% by weight, and most preferably at most 80% by weight ethylenically unsaturated compounds without acid functionality, based on the total weight of the unfilled composition.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[β-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone (meth) acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments photopolymerizable components include PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and NPGDMA (neopentylglycol dimethacrylate). Various combinations of the polymerizable components can be used if desired.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. Publication No. 2003/0166737 (Dede et al.).

Other suitable photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

Chemically Polymerizable Compositions

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, the reducing agent is present in an amount of at least 0.01% by weight, and more preferably at least 0.1% by weight, based on the total weight (including water) of the components of the polymerizable composition. Preferably, the reducing agent is present in an amount of no greater than 10% by weight, and more preferably no greater than 5% by weight, based on the total weight (including water) of the components of the polymerizable composition.

Preferably, the oxidizing agent is present in an amount of at least 0.01% by weight, and more preferably at least 0.10% by weight, based on the total weight (including water) of the components of the polymerizable composition. Preferably, the oxidizing agent is present in an amount of no greater than 10% by weight, and more preferably no greater than 5% by weight, based on the total weight (including water) of the components of the polymerizable composition.

The reducing or oxidizing agents can be microencapsulated as described in U.S. Pat. No. 5,154,762 (Mitra et al.). This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a photopolymerizable composition such as described U.S. Pat. No. 5,154,762 (Mitra et al.).

In some embodiments, dental compositions of the present invention including a hardenable resin can be hardened to fabricate a dental article selected from the group consisting of crowns, fillings, mill blanks, orthodontic devices, and prostheses.

Water-Dispersible Polymeric Film Former

In some embodiments, water-dispersible polymeric film formers as disclosed herein include a repeating unit that includes a polar or polarizable group as described herein below. In certain embodiments, the water-dispersible polymeric film formers also include a repeating unit that includes a fluoride releasing group, a repeating unit that includes a hydrophobic hydrocarbon group, a repeating unit that includes a graft polysiloxane chain, a repeating unit that includes a hydrophobic fluorine-containing group, a repeating unit that includes a modulating group, or combinations thereof, as described herein below. In some embodiments, the polymer optionally includes a reactive group (e.g., ethylenically unsaturated groups, epoxy groups, or silane moieties capable of undergoing a condensation reaction). Exemplary water-dispersible polymeric film formers are disclosed, for example, in U.S. Pat. No. 5,468,477 (Kumar et al.), U.S. Pat. No. 5,525,648 (Aasen et al.), U.S. Pat. No. 5,607,663 (Rozzi et al.), U.S. Pat. No. 5,662,887 (Rozzi et al.), U.S. Pat. No. 5,725,882 (Kumar et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.).

Repeating units including a polar or polarizable group are derived from vinylic monomers such as acrylates, methacrylates, crotonates, itaconates, and the like. The polar groups can be acidic, basic or salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B), ionic groups (such as quarternary ammonium, carboxylate salt, sulfonic acid salt and the like), and the precursors and protected forms of these groups. Additionally, a polar or polarizable group could be a macromonomer. More specific examples of such groups follow.

Polar or polarizable groups may be derived from mono- or multifunctional carboxyl group containing molecules represented by the general formula:

$$CH_2=CR^2G\text{-}(COOH)_d$$

where $R^2$=H, methyl, ethyl, cyano, carboxy or carboxymethyl, d=1-5 and G is a bond or a hydrocarbyl radical linking group containing from 1-12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid, and N-acryloyl glycine.

Polar or polarizable groups may, for example, be derived from mono- or multifunctional hydroxy group containing molecules represented by the general formula:

$$CH_2=CR^2-CO-L-R^3-(OH)_d$$

where $R^2$=H, methyl, ethyl, cyano, carboxy or carboxyalkyl, L=O, NH, d=1-5 and $R^3$ is a hydrocarbyl radical of valence d+1 containing from 1-12 carbon atoms. The preferred monomers in this class are hydroxyethyl (meth)acrylate, hydroxypropyl (meth)acrylate, hydroxybutyl (meth)acrylate, glycerol mono(meth)acrylate, tris(hydroxymethyl)ethane monoacrylate, pentaerythritol mono(meth)acrylate, N-hydroxymethyl (meth)acrylamide, hydroxyethyl (meth)acrylamide, and hydroxypropyl (meth)acrylamide.

Polar or polarizable groups may alternatively be derived from mono- or multifunctional amino group containing molecules of the general formula:

$$CH_2=CR^2-CO-L-R^3-(NR^4R^5)_d$$

where $R^2$, L, $R^3$, and d are as defined above and $R^4$ and $R^5$ are H or alkyl groups of 1-12 carbon atoms or together they constitute a carbocyclic or heterocyclic group. Preferred monomers of this class are aminoethyl (meth)acrylate, aminopropyl (meth)acrylate, N,N-dimethylaminoethyl (meth)acrylate, N,N-diethylaminoethyl (meth)acrylate, N,N-dimethylaminopropyl (meth)acrylamide, N-isopropylaminopropyl (meth)acrylamide, and 4-methyl-1-acryloyl-piperazine.

Polar or polarizable groups may also be derived from alkoxy substituted (meth)acrylates or (meth)acrylamides such as methoxyethyl (meth)acrylate, 2-(2-ethoxyethoxy) ethyl (meth)acrylate, polyethylene glycol mono(meth)acrylate or polypropylene glycol mono(meth)acrylate.

Polar or polarizable groups units may be derived from substituted or unsubstituted ammonium monomers of the general formula:

$$CH_2=CR^2-CO-L-R^3-(NR^4R^5R^6)_d Q^-$$

where $R^2$, $R^3$, $R^4$, $R^5$, L and d are as defined above, and where $R^6$ is H or alkyl of 1-12 carbon atoms and $Q^-$ is an organic or inorganic anion. Preferred examples of such monomers include 2-N,N,N-trimethylammonium ethyl (meth)acrylate, 2-N,N,N-triethylammonium ethyl (meth)acrylate, 3-N,N,N-trimethylammonium propyl (meth)acrylate, N(2-N',N',N'-trimethylammonium) ethyl (meth)acrylamide, N-(dimethyl hydroxyethyl ammonium) propyl (meth)acrylamide, or combinations thereof, where the counterion may include fluoride, chloride, bromide, acetate, propionate, laurate, palmitate, stearate, or combinations thereof. The monomer can also be N,N-dimethyl diallyl ammonium salt of an organic or inorganic counterion.

Ammonium group containing polymers can also be prepared by using as the polar or polarizable group any of the amino group containing monomer described above, and acidifying the resultant polymers with organic or inorganic acid to a pH where the pendant amino groups are substantially protonated. Totally substituted ammonium group containing polymers may be prepared by alkylating the above described amino polymers with alkylating groups, the method being commonly known in the art as the Menschutkin reaction.

Polar or polarizable groups can also be derived from sulfonic acid group containing monomers, such as vinyl sulfonic acid, styrene sulfonic acid, 2-acrylamido-2-methyl propane sulfonic acid, allyloxybenzene sulfonic acid, and the like.

Alternatively, polar or polarizable groups may be derived from phosphorous acid or boron acid group-containing monomers. These monomers may be used in the protonated acid form as monomers and the corresponding polymers obtained may be neutralized with an organic or inorganic base to give the salt form of the polymers.

Preferred repeating units of a polar or polarizable group include acrylic acid, itaconic acid, N-isopropylacrylamide, or combinations thereof.

In certain embodiments, the water-dispersible polymeric film formers disclosed herein also include a repeating unit that includes a fluoride releasing group. A preferred fluoride releasing group includes tetrafluoroborate anions as disclosed, for example, in U.S. Pat. No. 4,871,786 (Aasen et al.). A preferred repeating unit of a fluoride releasing group includes trimethylammoniumethyl methacrylate.

In certain embodiments, the water-dispersible polymeric film formers disclosed herein also include a repeating unit that includes a hydrophobic hydrocarbon group. An exemplary hydrophobic hydrocarbon group is derived from an ethylenically unsaturated preformed hydrocarbon moiety having a weight average molecular weight greater than 160. Preferably the hydrocarbon moiety has a molecular weight of at least 160. Preferably the hydrocarbon moiety has a molecular weight of at most 100,000, and more preferably at most 20,000. The hydrocarbon moiety may be aromatic or non-aromatic in nature, and optionally may contain partially or fully saturated rings. Preferred hydrophobic hydrocarbon moieties are dodecyl and octadecyl acrylates and methacrylates. Other preferred hydrophobic hydrocarbon moieties include macromonomers of the desired molecular weights prepared from polymerizable hydrocarbons, such as ethylene, styrene, alpha-methyl styrene, vinyltoluene, and methyl methacrylate.

In certain embodiments, the water-dispersible polymeric film formers disclosed herein also include a repeating unit that includes a hydrophobic fluorine containing group. Exemplary repeating units of hydrophobic fluorine-containing groups include acrylic or methacrylic acid esters of 1,1-dihydroperfluoroalkanols and homologs: $CF_3(CF_2)_x CH_2 OH$ and $CF_3(CF_2)_x(CH_2)_y OH$, where x is zero to 20 and y is at least 1 up to 10; ω-hydrofluoroalkanols $(HCF_2(CF_2)_x(CH_2)_y OH)$, where x is 0 to 20 and y is at least 1 up to 10; fluoroalkylsulfonamido alcohols; cyclic fluoroalkyl alcohols; and $CF_3 (CF_2CF_2O)_q(CF_2O)_x(CH_2)_y OH$, where q is 2 to 20 and greater than x, x is 0 to 20, and y is at least 1 up to 10.

Preferred repeating units of a hydrophobic fluorine-containing group include 2-(methyl(nonafluorobutyl)sulfonyl) amino)ethyl acrylate, 2-(methyl(nonafluorobutyl)sulfonyl) amino)ethyl methacrylate, or combinations thereof.

In certain embodiments, the water-dispersible polymeric film formers disclosed herein also include a repeating unit that includes a graft polysiloxane chain. The graft polysiloxane chain is derived from an ethylenically unsaturated preformed organosiloxane chain. The molecular weight of this unit is generally above 500. Preferred repeating units of a graft polysiloxane chain include a silicone macromer.

Monomers used to provide the graft polysiloxane chain of this invention are terminally functional polymers having a single functional group (vinyl, ethylenically unsaturated, acryloyl, or methacryloyl group) and are sometimes termed macromonomers or "macroiners". Such monomers are known and may be prepared by methods as disclosed, for example, in U.S. Pat. No. 3,786,116 (Milkovich et al.) and U.S. Pat. No. 3,842,059 (Milkovich et al.). The preparation of polydimethylsiloxane macromonomer and subsequent copolymerization with vinyl monomer have been described in several papers by Y. Yamashita et al., [Polymer J. 14, 913 (1982); ACS Polymer Preprints 25 (1), 245 (1984); Makromol. Chem. 185, 9 (1984)].

In certain embodiments, the water-dispersible polymeric film formers disclosed herein also include a repeating unit that includes a modulating group. Exemplary modulating groups are derived from acrylate or methacrylate or other vinyl polymerizable starting monomers and optionally contain functionalities that modulate properties such as glass transition temperature, solubility in the carrier medium, hydrophilic-hydrophobic balance and the like.

Examples of modulating groups include the lower to intermediate methacrylic acid esters of 1-12 carbon straight, branched or cyclic alcohols. Other examples of modulating groups include styrene, vinyl esters, vinyl chloride, vinylidene chloride, acryloyl monomers and the like.

Preferred film formers are acrylate-based copolymers and urethane polymers such as the AVALURE series of compounds (e.g., AC-315 and UR-450), and carbomer-based polymers such as the CARBOPOL series of polymers (e.g., 940NF), all available from Noveon, Inc., Cleveland, Ohio.

Optional Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, tartaric acid, chelating agents, buffering agents, stabilizers, and other similar ingredients that will be apparent to those skilled in the art. Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Methods of Use

Exemplary methods of using compositions of the present invention are described in the Examples. In some embodiments of the present invention, dental compositions of the present invention can be contacted with a tooth structure to treat the tooth structure. In some embodiments, placing a dental composition according to the present invention in an oral environment can effect remineralization, reduction of sensitivity, and/or protection of the tooth structure. In preferred embodiments, placing a dental composition according to the present invention in an oral environment delivers ions (e.g., calcium, phosphorus, and/or fluorine containing ions) to the oral environment.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Visual Opacity (MacBeth Values) Test Method

Disc-shaped (1-mm thick×15-mm diameter) paste samples were cured by exposing them to illumination from a VISILUX 2 curing light (3M Company, St. Paul, Minn.) for 60 seconds on each side of the disk at a distance of 6 mm. Hardened samples were measured for direct light transmission by measuring transmission of light through the thickness of the disk using a MacBeth transmission densitometer Model TD-903 equipped with a visible light filter, available from MacBeth (MacBeth, Newburgh, N.Y.). Lower MacBeth Values indicate lower visual opacity and greater translucency of a material. The reported values are the average of 3 measurements.

Compressive Strength (CS) Test Method

Compressive strength of a test sample was measured according to ANSI/ASA specification No. 27 (1993). A sample was packed into a 4-mm (inside diameter) glass tube; the tube was capped with silicone rubber plugs; and then the tube was compressed axially at approximately 0.28 MPa for 5 minutes. The sample was then light cured for 90 seconds by exposure to two oppositely disposed VISILUX Model 2500 blue light guns (3M Co., St. Paul, Minn.), followed by irradiation for 180 seconds in a Dentacolor XS unit (Kulzer, Inc., Germany). Cured samples were cut with a diamond saw to form 8-mm long cylindrical plugs for measurement of compressive strength. The plugs were stored in distilled water at 37° C. for 24 hours prior to testing. Measurements were carried out on an Instron tester (Instron 4505, Instron Corp., Canton, Mass.) with a 10 kilonewton (kN) load cell at a crosshead speed, of 1 mm/minute. Five cylinders of cured samples were prepared and measured with the results reported in MPa as the average of the five measurements.

Diametral Tensile Strength (DTS) Test Method

Diametral tensile strength of a test sample was measured according to ANSI/ASA specification No. 27 (1993). Samples were prepared as described for the CS Test Method, except that the cured samples were then cut into 2.2-mm thick disks for measurement of DTS. The disks were stored in water as described above and measured with an Instron tester (Instron 4505, Instron Corp.) with a 10 (kN) load cell at a crosshead speed of 1 mm/minute. Five disks of cured samples were prepared and measured with results reported in MPa as the average of the five measurements.

Work Time (WT) Test Method

The working time for a mixed cement to solidify was measured according to the following procedure. The tools and pastes were stored before use in a constant temperature and humidity room (22° C. and 50% RH) and the procedure was conducted in the same room. Selected amounts of A and B pastes were mixed by a spatula on a pad for 25 seconds (sec) and the resulting mixed composition sample transferred into the semi-cylindrical trough section (8-cm long, 1-cm wide and 3-mm deep) of an 8-cm by 10-cm plastic block. At time 1:00 min, perpendicular grooves were made using a ball point (1-mm diameter) groove maker across the trough every 30 sec; at 2:00 min, the grooves were made every 15 sec; and, closer to the end of the working time, the grooves were made every 10 sec. The end of the working time was determined when the lumps of the cement sample moved with the groove maker. The working time was reported as the average of 2 or 3 measurements.

Spectral Opacity (SO) Test Method

ASTM-D2805-95 was modified to measure the spectral opacity for dental materials with thicknesses of approximately 1.0 mm. Disk-shaped, 1-mm thick by 20-mm diameter samples were cured by exposing them to illumination from a 3M Visilux-2 dental curing light for 60 seconds on each side of the disk at a distance of 6 mm. Y-tristimulus values for the disks were measured on an Ultrascan XE Colorimeter with a ⅜ inch aperture (Hunter Associates Labs, Reston, Va.) with separate white and black backgrounds. The D65 Illuminant was used with no filters for all measurements. A 10-degree angle of view was used. The Y-tristimulus values for the white and black substrates were 85.28 and 5.35, respectively. The spectral opacity is calculated as the ratio of the reflectance of a material on a black substrate to that of an identical material on a white substrate. Reflectance is defined as equal to the Y-tristimulus value. Thus, spectral opacity=$R_B/R_W$, where $R_B$=reflectance of a disk on a black substrate and $R_W$=reflectance of the same disk on a white substrate. Spectral opacity is unitless. Lower spectral opacity values indicate lower visual opacity and greater translucency of a material.

Adhesion to Dentin (AD) and Enamel (AE) Test Methods

Adhesion to dentin and adhesion to enamel were measured according to the procedure described in U.S. Pat. No. 6,613,812 (Bui et al.), except that a light cure exposure time of 20 seconds was used and 3M ESPE Filtek Z250 composite was used instead of 3M Z100 Restorative.

For primer compositions, AD and AE were measured as above, except that the primer composition was swabbed on a moist bovine tooth surface for 20 sec, gently air-dried 5-10 sec, and then light-cured 10 sec; and Vitremer Core Restorative was used instead of the Filtek Z250 composite.

X-Ray Diffraction (XRD) Test Method

A test sample was mulled in a boron carbide mortar and applied as an ethanol slurry to a zero background specimen holder (aluminum holder with quartz insert). Reflection geometry data were collected in the form of survey scans using a Philips vertical diffractometer, copper K$\alpha$ radiation, and proportional detector registry of the scattered radiation. The crystallite sizes (D) for the crystalline phases present were calculated from observed peak widths after correction for instrumental broadening as the full width at half maximum using a Pearson VII peak shape model, accounting for $\alpha 1/\alpha 2$ separation.

Calcium and Phosphorus Ion Release (CIR) Test Method

Disk-shaped, 1-mm thick by 20-mm diameter samples were cured by exposing them to illumination from a 3M XL3000 dental curing light for 60 seconds on each side of the disk at a distance of 6 mm. The disks were stored in a HEPES-buffered solution at 37° C.; the solution was exchanged periodically, and the ion content measured via inductively coupled plasma spectroscopy (ICP) on a Perkin-Elmer 3300DV Optima ICP unit or via a calcium-selective electrode. The composition of the buffer solution was 1000 g deionized water, 3.38 g NaCl, and 15.61 g HEPES (N-2-hydroxyethylpiperazine-N'-2-ethanesulfonic acid). The ion release rate, microgram (ion)/g(disk)/day, was calculated by dividing the total ion content of the solution (concentration times volume of solution) by the initial disk weight and by the time in days since the last exchange of buffer solution.

Enamel Remineralization Test Method

This method was carried out as described in "Surface Modulation of Dental Hard Tissues" (D. Tantbirojn, Ph.D. thesis, University of Minnesota, 1998), with the following exceptions. The demineralizing solution was 0.1 ppm $F^-$ from NaF, 1.5 mM $Ca^{+2}$ from $CaCl_2$, 0.9 mM $PO4^{-3}$ from $KH_2PO_4$, 50 mM acetic acid, adjusted to pH=5.0 with 1M KOH; and the mineral content was measured by quantitative image analysis of microradiographs.

Dentin Remineralization Test Method

This method was carried out as described in "Surface Modulation of Dental Hard Tissues" (D. Tantbirojn, Ph.D. thesis, University of Minnesota, 1998), with the following exceptions. Dentin was used instead of enamel; the demineralizing solution was 0.1 ppm $F^-$ from NaF, 1.5 mM $Ca^{+2}$ from $CaCl_2$, 0.9 mM $PO4^{-3}$ from $KH_2PO_4$, 50 mM acetic acid, adjusted to pH=5.0 with 1M KOH; and the mineral content was measured by quantitative image analysis of microradiographs.

Resistance to Demineralization in Dentin Test Method

This method was carried out as described in "Surface Modulation of Dental Hard Tissues" (D. Tantbirojn, Ph.D. thesis, University of Minnesota, 1998), with the following exceptions. Dentin was used instead of enamel; the demineralizing solution was 0.1 ppm $F^-$ from NaF, 1.5 mM $C+^2$ from $CaCl_2$, 0.9 mM PO4-3 from $KH_2PO_4$, 50 mM acetic acid, adjusted to pH=5.0 with 1M KOH; and the extent of acid erosion adjacent to the sample was qualitatively categorized from microradiographs.

Abbreviations, Descriptions, and Sources of Materials

| Abbreviation | Description and Source of Material |
|---|---|
| BisGMA | 2,2-Bis[4-(2-hydroxy-3-methacryloyloxypropoxy)phenyl]propane CAS No. 1565-94-2 |
| TEGDMA | Triethyleneglycol dimethacrylate (Sigma-Aldrich, St. Louis, MO) |
| PEGDMA-400 | Polyethyleneglycol dimethacrylate (Sartomer 603; MW about 570; Sartomer, Exton, PA) |
| HEMA | 2-Hydroxyethyl methacrylate (Sigma-Aldrich) |
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity $\rho$ = 4.64. |
| IEM | 2-Isocyanatoethyl methacrylate (Sigma-Aldrich) |
| VBP | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| PM-2 | KAYAMER PM-2; Bis(methacryloxyethyl) phosphate (Nippon Kiyaku, Japan) |
| MHP | Methacryloyloxyhexyl phosphate (See Preparation Method described herein) |
| CPQ | Camphorquinone (Sigma-Aldrich) |
| EDMAB | Ethyl 4-(N,N-dimethylamino)benzoate (Sigma-Aldrich) |
| DPIHFP | Diphenyl Iodonium Hexafluorophosphate (Johnson Matthey, Alpha Aesar Division, Ward Hill, NJ) |
| BHT | 2,6-di-tert-butyl-4-methylphenol (Sigma-Aldrich) |
| Filler B | Nano-sized silica and zirconia particles loosely aggregated as substantially amorphous clusters were prepared in the form of a dry powder filler according to the procedure for "Cluster particles filler" in Column 22 of U.S. Pat. No. 6,572,693 (Wu et al.); except that the filler was not silane-treated and there was an additional firing step (550° C. for 4 hours) after milling. |
| Filler C | Silane-treated fluoroaluminosilicate glass filler prepared as described for Filler B in U.S. Pat. Publication No. 2003/0198914 (Brennan et al.) |

-continued

| Abbreviation | Description and Source of Material |
|---|---|
| Filler D | Silane-treated, nano-sized silica and zirconia particles loosely aggregated as substantially amorphous clusters were prepared in the form of a dry powder filler according to the procedure for "Cluster particles filler" in Column 22 of U.S. Pat. No. 657,572,693 (Wu et al.). |
| Filler E | Schott Glass Product No. G 018-117 (Schott Electronic Packaging, GmbH, Landshut, Germany). The filler was silane-treated as described for Filler FAS VI in U.S. Pat. Publication No. 2003/0166740 (Mitra et al.). |
| Filler F | Silane-treated nanozirconia prepared according to the procedure for Preparatory Example 1A in U.S. patent application Ser. No. 10/847,781, filed May 17, 2004 (Kangas et al.) |
| Filler G | Silane-treated, non-aggregated, nano-sized silica particles in the form of a dry powder were prepared according to the procedure for Filler A in U.S. Pat. Publication No. 2003/0181541 (Wu et al.), except that Nalco 2327 was used in place of Nalco 2329. The nominal particle size of this filler was assumed to be the same as in the starting Nalco 2327 silica sol, i.e., about 20 nanometers. |
| Filler H | Silane-treated, non-aggregated, nano-sized silica particles in the form of a dry powder were prepared according to the procedure for Filler A in U.S. Pat. Publication No. 2003/0181541 (Wu et al.). The nominal particle size of this filler was assumed to be the same as in the starting Nalco 2329 silica sol, i.e., about 75 nanometers. |
| PHOSCAL | Caseinate material comprising a casein phosphoprotein-calcium phosphate complex. (NSI Dental, Australia) |
| Sodium Caseinate | Sodium salt of casein comprising a calcium phosphate complex (ICN Biomedicals, Aurora, OH) |
| Nalco 1042 | Acidic colloidal silica sol (Nalco Corp., Naperville, IL) |
| Nalco 2329 | Sodium hydroxide stabilized colloidal silica sol (Nalco Corp.) |
| Nalco 2326 | Colloidal silica sol (Nalco Corp.) |
| Vitrebond Powder | Powder component of VITREBOND Light Cure Glass Ionomer Liner/Base (3M Company, St. Paul, MN) |
| Vitrebond Liquid/Resin | Liquid component of VITREBOND Light Cure Glass Ionomer Liner/Base (3M Company) |
| Vitremer Liquid/Resin | Liquid resin component of VITREMER Restorative (3M Company) |
| Vitremer Primer | Liquid primer component packaged with VITREMER Core Build-Up/Restorative (3M Company) |
| Filtek Z250 Resin | Resin component of FILTEK Z250 Universal Restorative System (3M Company) |
| F2000 Resin | Resin component of F2000 Compomer Restorative System (3M Company) |
| AC-315 | AVALURE acrylate-based copolymer (Noveon, Inc., Cleveland, OH) |
| 940NF | CARBOPOL carbomer-based polymer (Noveon, Inc.) |
| UR-450 | AVALURE urethane polymer (Noveon, Inc.) |

Starting Materials Preparations

6-Methacryloyloxyhexyl Phosphate (MHP)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous $Na_2SO_4$ then isolated by vacuum filtration to give 1067 g (67.70%) of 6-hydroxyhexyl methacrylate, a yellow oil. This desired product was formed along with 15-18% of 1,6-bis (methacryloyloxyhexane). Chemical characterization was by NMR analysis.

6-Methacryloyloxyhexyl Phosphate (MHP) Synthesis: A slurry was formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloyloxyhexyl Phosphate (MHP) as a yellow oil. Chemical characterization was by NMR analysis.

Resins A, B, C, D and E

Resins A, B, C, D and E were prepared by combining the ingredients as shown in Table 1.

TABLE 1

Compositions of Resins A, B, C, D and E

| Ingredient (Weight %) | Resin A | Resin B | Resin C | Resin D | Resin E |
|---|---|---|---|---|---|
| VBP | 43.43 | 43.00 | 0 | 0 | 0 |
| HEMA | 22.27 | 22.05 | 17.00 | 0 | 0 |
| BisEMA6 | 0 | 0 | 0 | 32.00 | 37.13 |
| BisGMA | 0 | 0 | 27 | 0 | 0 |
| TEGDMA | 0 | 0 | 38 | 32.00 | 60.00 |
| MHP | 0 | 0 | 14.34 | 0 | 0 |
| PM-2 | 0 | 0 | 0 | 33.15 | 0 |
| Water | 34.04 | 33.70 | 0 | 0 | 0 |
| CPQ | 0.30 | 0.30 | 0.32 | 0.3 | 0.3 |
| DPIHFP | 0 | 1.00 | 0.53 | 0 | 0 |
| BHT | 0.05 | 0.05 | 0.39 | 0.15 | 0.17 |
| EDMAB | 0 | 0 | 2.42 | 2.4 | 2.4 |
| TOTAL: | 100 | 100 | 100 | 100 | 100 |

Examples 1A and 1B

Zirconia-Silica Nanocluster Fillers Treated with Caseinate Materials

Example 1A

Filler B (nanocluster zirconia-silica) (149.3 g) was stirred into a solution of 10% by weight Sodium Caseinate (213.4 g) to form a smooth, creamy slurry. To this slurry was added sequentially a solution of 10% by weight $Na_2HPO_4$ in deionized water (35.4 g); additional deionized water (57 g); a solution of 3.9% by weight NaOH in deionized water (57 g) to adjust the Ph from about 6.5 to about 9.0; and a solution of 46.4% by weight $CaCl_2.2H_2O$ in deionized water (35.4 g) to yield a homogeneous dispersion with no gelation or settling. This dispersion was dried on a gap dryer to yield thin flakes approximately 2-10 mm across, which were extremely friable and readily crushed to a fine powder (designated Example 1). The final powder had a calculated composition of 20% calcium-phosphate-caseinate and 80% Filler B. Powder X-Ray Diffraction (XRD) showed that the powder was largely amorphous, with peaks for NaCl (crystallite size≧1500 Å, relative peak size 100) and monoclinic zirconia (crystallite size 30 Å, relative peak size 36). For comparison, the XRD pattern of the as-received Sodium Caseinate showed a notable difference in the shape of the broad amorphous peaks. The Sodium Caseinate had a major broad peak at d=4.3778 Å and an additional broad peak at d=9.4020 Å, possibly indicative of a disordered crystalline structure. Example 1A, by contrast, had a major broad peak at d=3.8415 Å (significantly shifted compared to the Sodium Caseinate), and no peaks at higher d-spacings; this pattern is indicative of an amorphous material.

Example 1B

Filler B (45.1 g) was mixed with deionized water (59.4 g) and PHOSCAL (5.2 g) to form a thin, smooth, homogeneous slurry. The slurry was gap-dried on the same day to yield thin, friable flakes that crushed readily to a powder. The final powder (designated Example 1B) contained 10% PHOSCAL and 90% Filler B.

Examples 2A-2C

Silica Nanocluster Fillers Treated with Caseinate Materials

Example 2A

Nalco 2329 colloidal silica sol (89.6 g) was stirred into a solution of 10% by weight Sodium Caseinate (213.4 g) to form a thin, turbid sol. To this sol was added sequentially a solution of 10% by weight $Na_2HPO_4$ in deionized water (28.0 g); a solution of 3.9% by weight NaOH in deionized water (9.7 g) to adjust the Ph from about 7.4 to about 9.5; and a solution of 46.4% by weight $CaCl_2.2H_2O$ in deionized water (7.2 g). After a short period of time, some white gelatinous globs appeared. This sol was refrigerated overnight, and then dried on a gap dryer the next day to yield thin flakes which were extremely friable and readily crushed to a fine powder (designated Example 2A). The white precipitates caused some difficulties in the gap dryer.

Example 2B

Nalco 2329 colloidal silica sol (154 g) was stirred into a solution of 10% by weight Sodium Caseinate (213.4 g) to form a thin, turbid sol. To this sol was added sequentially a solution of 10% by weight $Na_2HPO_4$ in deionized water (9.8 g); a solution of 3.9% by weight NaOH in deionized water (7.0 g) to adjust the Ph from about 7.4 to about 9.5; and a solution of 46.4% by weight $CaCl_2.2H_2O$ in deionized water (2.5 g) to yield a stable, homogeneous sol with no precipitates, separation, or gelation. This sol was refrigerated overnight, and then dried on a gap dryer the next day to yield large, thin flakes which were extremely friable and readily crushed to a fine powder (designated Example 2B). XRD showed that the powder was largely amorphous, with peaks only for NaCl (crystallite size 1305 Å) evident. There was a single major broad peak at d~4.0 Å, with no peaks at higher d-spacings; this XRD pattern was similar to the XRD pattern for Example 1A. Scanning Electron Microscopy (SEM) and Transmission Electron Microscopy (TEM) images of Example 2B showed that the spherical colloidal silica particles were bound together in clusters by the caseinate.

Example 2C

PHOSCAL (6.0 g) was dissolved into Nalco 2326 colloidal silica (92.2 g) to form a thin, homogeneous, slightly turbid sol. The sol was gap-dried on the same day, yielding coarse, friable granules whose net composition was 30% PHOSCAL and 70% silica. The granules were friable and readily crushed to a fine powder (designated Example 2C). Powder XRD of PHOSCAL revealed a broad peak structure (at about d~4.3 Å and d~9.6 Å) similar to the XRD pattern for Sodium Caseinate (see Example 1A), with additional nanocrystalline peaks at d=2.8 Å from NaCl, and at d=3.4 Å that might be a calcium phosphate phase. Example 2C, by contrast, had a broad peak at d~3.9 Å, and a very small peak at d~9.8 Å (much smaller than in the PHOSCAL pattern). The broad peak at d=2.8 Å (NaCl) was much smaller in the Example 2C pattern than in the PHOSCAL pattern and there were no peaks at about d=3.4 Å.

Example 3

Oven-Dried Caseinate (PHOSCAL)

A solution of 12% PHOSCAL in deionized water was dried in a glass tray at 100° C. for 3 hours. In another experiment, the PHOSCAL solution was dried as above and then further heated at 140° C. for 15 hours. XRD patterns of the as-received, dried, and dried/heated PHOSCAL powder materials had the same broad peak structure (peaks at about d~4.3 Å and d~9.6 Å). Moreover, the XRD pattern for the dried material lacked the nanocrystalline peak at d=3.4 Å (θ~28°); this peak is present in the XRD pattern for the dried/heated material which was heated at higher temperatures for much longer times. Thus, conventional oven drying did not impart the unique structure seen in the inventive materials (e.g. Examples 1A and 2C), which lacked the broad peak at d~9.6 Å. These experiments demonstrate that the inventive processes can impart a unique structure to the caseinate materials.

PHOSCAL—General Solubility Properties

PHOSCAL dissolved readily in water at up to 16% by weight to form a cloudy, stable solution; at 16% a thick liquid was formed; and at 20% a soft gel was formed.

PHOSCAL dispersed into, but did not dissolve in ethanol or in certain methacrylate resins (e.g., HEMA, FILTEK Z250 resin, and certain resins containing phosphorylated components).

PHOSCAL was mixed into ethanol at 0.1%, 1.0%, 2.0%, and 8.0% with essentially no solubility observed. After 7 months aging under ambient conditions, the PHOSCAL readily dispersed within the ethanol with agitation. Similar results were observed for PHOSCAL in a methacrylate resin (FILTEK Z250 resin) at 0.1% to 4.0% and in HEMA at 2.0%.

PHOSCAL at 6.2% blended into an 80/20 ethanol/deionized water (DIW) solution to form a white, gelatinous lump. However, PHOSCAL at 8% solution in DIW (0.8 g) blended with ethanol (1.0 g) to form a cloudy, stable solution. Thus the order of addition affected the solubility results in some cases.

Examples 4A-4F

Glass Filler Treated with Caseinate Materials

Vitrebond Powder (glass filler) was slurried with ethanol followed by the addition of a caseinate material and the resulting mixture blended thoroughly to form a creamy, homogeneous slurry. The slurry was either gap-dried or dried in a PYREX tray at 80° C. for 4 hours in a convection oven. The compositions prepared and observations of the dried materials are provided in Table 2.

TABLE 2

| Example | Caseinate % | Drying Method | Comment |
|---|---|---|---|
| 4A | 1% Phoscal | Tray-dried | Friable cake, easily crushed to powder |
| 4B | 5% Phoscal | Tray-dried | Friable cake, easily crushed to powder |
| 4C | 5% Sodium Caseinate | Tray-dried | Friable cake, easily crushed to powder |
| 4D | 10% Phoscal | Tray-dried | Hard cake, crushed in mortar & pestle to powder |
| 4E | 2% Phoscal | Tray-dried | Friable cake, easily crushed to powder |
| 4F | 10% Phoscal | Gap-dried | Friable flakes |

Examples 5A-5B and Comparative Examples (CE) 1-3

Stability of Silica Nanoparticles Treated with a Caseinate Material (PHOSCAL)

The stability of compositions containing VBP, colloidal silica (Nalco 1042), and PHOSCAL (Examples 5A-5B) were compared to similar compositions that lacked either the colloidal silica or the PHOSCAL (Comparative Examples 1-3). The PHOSCAL, if present, was first dissolved in the water before blending into the final composition. All compositions were aged in glass vials under ambient conditions. The compositions (values are weight %) and observations at 7-months ageing are provided in Table 3. Only the compositions containing both colloidal silica nanoparticles and PHOSCAL were found to be stable at 7 months.

In a separate experiment, the sodium monofluorophosphate ($Na_2FPO_3$) was shown to cause the Nalco 1042 to gel. Thus, the presence of the caseinate material PHOSCAL appeared to stabilize the Nalco 1042 in the presence of the sodium monofluorophosphate.

In another experiment, varying levels of PHOSCAL (0.1, 1, 2, and 4%) were mixed into a solution of 50% VBP, 40% EtOH, 10% Nalco 1042 to form cloudy solutions. All solutions remained as homogeneous, cloudy, and stable through 7 months under ambient conditions.

TABLE 3

| Example | VBP | EtOH | DI Water | Nalco 1042 | PHOSCAL | $Na_2FPO_3$ | Appearance at 7 months |
|---|---|---|---|---|---|---|---|
| 5A | 41.7 | 33.3 | 14.7 | 8.3 | 2 | 0 | Homogeneous; no precipitation, gelation, separation |
| CE 1 | 45.3 | 36.3 | 7.9 | 9.1 | 0 | 1.5 | Separation; rubbery gel |
| CE 2 | 44.9 | 35.9 | 18.0 | 0 | 1.2 | 0 | Separation |
| CE 3 | 45.2 | 36.2 | 17.1 | 0 | 0 | 1.6 | Separation; rubbery gel |
| 5B | 43.5 | 34.8 | 11.3 | 8.7 | 1 | 0.7 | Homogeneous; no precipitation, gelation, separation |

Examples 6-13 and Comparative Examples 4-5

RMGI Compositions Containing a Caseinate (PHOSCAL)

The caseinate material PHOSCAL (included in Powder 2) was mixed with Vitrebond Powder (Powder 1 or Powder 2 component) and then with various liquid resins to afford homogeneous RMGI pastes designated Examples 6-13. These pastes were evaluated for compressive strength (CS), diametral tensile strength (DTS), work time, spectral opacity, and adhesion to dentin (AD) according to the Test Methods described herein and the results compared to those from the commercial VITREBOND (VB) Light Cure Glass Ionomer Liner/Base product (Comparative Examples (CE) 4 and 5). (For the AD tests of these materials, an additional step was added: a dental adhesive (3M ESPE Singlebond Plus dental adhesive) was brushed over the cured material and then light-cured for 10 sec before application of the composite.) The paste compositions are provided in Table 4A and the evaluation results in Table 4B.

TABLE 4A

| Example | Powder 1 (P1) | Powder 2 (P2) | Liquid Resin (L) | P1/P2/L (Weight Ratio) |
|---|---|---|---|---|
| CE 4 | Vitrebond | None | Vitrebond | 1.4/0/1 |
| CE 5 | Vitrebond | None | Vitrebond | 1/0/1 |
| 6 | | Example 4A | Resin B | 0/1/1 |
| 7 | | Example 4E | Resin B | 0/1/1 |
| 8 | Vitrebond | PHOSCAL | Vitrebond | .95/.05/1 |
| 9 | | Example 4B | Vitremer | 0/1/1 |
| 10 | Vitrebond | Example 1B | Resin B | 0.5/0.5:/1 |
| 11 | | Example 4F | Resin B | 0/1/1 |
| 12 | | Example 4D | Resin B | 0/1/1 |
| 13 | Vitrebond | Example 2C | Resin B | 0.9/0.1/1 |

TABLE 4B

| Example | Spectral Opacity | CS MPa (SD) | DTS MPa (SD) | Work Time Min:Sec | Dentin Adhesion MPa (SD) |
|---|---|---|---|---|---|
| CE 4 | 77.19 | 113 (9.5) | 25.3 (1.7) | 4:55 | 6.9 (5.6) |
| CE 5 | 80.60 | 104 (3) | 19.8 (4.2) | 5:05 | NT* |
| 6 | 78.05 | 88 (7) | 17.3 (3.1) | 5:05 | 9.7 (1.7) |
| 7 | NT | 84 (15) | 15.9 (2.7) | NT | 9.5 (1.2) |
| 8 | NT | 65 (5) | 11.6 (1.6) | NT | NT |
| 9 | 76.14 | 57 (5) | 10.8 (1.1) | 5:00 | 6.0 (2.7) |
| 10 | 74.22 | 86 (7) | 15.8 (1.6) | NT | 6.9 (1.6) |
| 11 | 72.51 | 36 (4) | 5.3 (1.0) | 4:40 | 4.1 (0.9) |
| 12 | 74.59 | 51 (3) | 10.4 (1.4) | 4:40 | 1.2 (1.3) |
| 13 | 72.62 | 91 (11) | 15.0 (1.2) | NT | NT |

*NT—Not Tested

Examples 14-16

Acidic Resin Compositions Containing a Caseinate (PHOSCAL)

Acidic resin compositions containing a caseinate (PHOSCAL) (Examples 14-16) were prepared by combining the ingredients shown in Table 5. The resulting paste compositions were evaluated for compressive strength (CS), diametral tensile strength (DTS), spectral opacity, and shear adhesion to dentin and enamel according to the Test Methods described herein and the results are provided in Table 5.

TABLE 5

| Example | Composition (Numbers are Weight %) | Spectral Opacity | CS MPa (SD) | DTS MPa (SD) | Dentin Adhesion MPa (SD) | Enamel Adhesion MPa (SD) |
|---|---|---|---|---|---|---|
| 14 | Resin D - 42<br>PHOSCAL - 8<br>Filler C - 15<br>Filler D - 35 | 51.46 | 183 (49) | 27.7 (9.1) | 3.1 (1.3) | 17.5 (5.7) |
| 15 | Resin D - 45<br>Filler C - 15<br>Example 1B - 40 | 66.48 | 192 (36) | 39.6 (4.7) | NT | NT |
| 16 | Resin D - 38<br>Filler C - 15<br>Filler D - 35<br>Example 2C - 12 | 60.46 | 215 (39) | 27.6 (14.1) | NT | NT |

Examples 17-19

Acidic Resin Compositions Containing a Caseinate Material

Acidic resin compositions containing a caseinate material were prepared by combining the ingredients listed below. The resulting paste compositions were evaluated in calcium and phosphorus ion release evaluations.

Example 17

Example 1A (55%), Vitremer Resin (45%)

Example 18

Example 1A (55%), Resin C (45%)

Example 19

Example 2B (55%), Vitremer Resin (45%)

Examples 20-22

Resin Compositions Containing a Caseinate (PHOSCAL)

PHOSCAL was soluble and stable in Resin B up to at least 16% by weight. The cloudiness and viscosity of the resulting resin increased with concentration. At less than 4%, the viscosity increase is minimal; at 8% the resin was much more viscous; and, at 16%, the resin was gelatinous. PHOSCAL in Resin B at 1%, 4% and 8% were designated Examples 20-22, respectively. PHOSCAL exhibited similar behavior in Vitremer Resin. All of the resulting resins remained stable through at least 7 months at ambient conditions and would be suitable for a variety of applications, including RMGI materials, adhesives, primers, and coatings.

Examples 23-25 and Comparative Examples 6-7

RMGI Compositions Containing a Caseinate (PHOSCAL)

Liquid resin Resin B) compositions containing PHOSCAL (Examples 20-22) were spatulated with Vitrebond Powder at a Powder/Liquid (P/L) ratio of 1.2/1 to afford homogeneous RMGI pastes designated Examples 23-25, respectively. These pastes were evaluated for compressive strength (CS), diametral tensile strength (DTS), work time, spectral opacity, and adhesion to dentin (AD) according to the Test Methods described herein and the results compared to those from the commercial VITREBOND Light Cure Glass Ionomer Liner/Base product (Comparative Examples (CE) 6 and 7). (For the AD tests of these materials, an additional step was added: a dental adhesive (3M ESPE Singlebond Plus dental adhesive) was brushed over the cured material and then light-cured for 10 sec before application of the composite.) The data are provided in Table 6 and show that the physical properties of the PHOSCAL (1%)-containing RMGI compositions were generally the same as for the commercial VITREBOND product, whereas the PHOSCAL (4% and 8%)-containing RMGI compositions showed significantly lower strength values.

TABLE 6

| Ex. | Powder | Liquid | P/L | Spectral Opacity | CS MPa (SD) | DTS MPa (SD) | Work Time Min:Sec | Dentin Adh. MPa (SD) |
|---|---|---|---|---|---|---|---|---|
| 23 | Vitrebond | Ex. 1 (1% PHOSCAL) | 1.2/1 | 76.2 | 99 (5) | 19.0 (4) | NT* | 5.7 (1.0) |
| 24 | Vitrebond | Ex. 2 (4% PHOSCAL) | 1.2/1 | 78.7 | 49 (4) | 8.2 (1) | 4.45 | 10.4 (3.6) |
| 25 | Vitrebond | Ex. 3 (8% PHOSCAL) | 1.2/1 | 76.4 | 34 (9) | NT | NT | NT |
| CE 6 | Vitrebond | Vitrebond | 1.4/1 | 77.2 | 113 (10) | 25.3 (1.7) | 4:55 | 6.9 (5.6) |
| CE 7 | Vitrebond | Vitrebond | 1/1 | 80.6 | 104 (3) | 19.8 (4.2) | 5.05 | NT |

*NT—Not Tested

Examples 26-29 and Comparative Example 8

Aqueous Resin Compositions Containing a Caseinate (PHOSCAL)

Primer Compositions

Table 7 provides the composition (weight % of ingredients) of aqueous polymerizable resin compositions containing PHOSCAL (Examples 26-29). These compositions were evaluated as primers for Vitremer Core Build-up/Restorative according to the Test Method described herein and the results (adhesion to dentin and enamel) compared to those from the commercial Vitremer Primer product (Comparative Example 8). (For the AE and AD tests of these materials, the primer was brushed on the tooth surface for 20 sec, gently air-dried for 10 sec, and then light-cured for 10 sec.) The data are provided in Table 8 and show that the compositions containing PHOSCAL had adhesion values approximately equivalent to Vitremer Primer.

TABLE 7

Resin Compositions Containing PHOSCAL (Ingredients in Weight %)

| Ex. | VBP | HEMA | EtOH | DIW | Nalco 1042 | PHOSCAL | $Ca(NO_3)_2 \cdot 4H_2O$ |
|---|---|---|---|---|---|---|---|
| 26 | 35 | 10 | 26 | 16 | 3 | 4 | 6 |
| 27 | 14 | 37 | 31.75 | 14.08 | 0 | 1.9 | 0 |
| 28 | 14 | 33.75 | 30 | 14.08 | 0 | 1.9 | 5 |
| 29 | 35 | 12 | 29.7 | 15 | 0 | 2 | 5 |

TABLE 8

| | Dentin Adhesion | | Enamel Adhesion | |
|---|---|---|---|---|
| Example | MPa | SD | MPa | SD |
| CE 8 | 9.9 | 5.3 | 8.9 | 1.6 |
| 26 | 5.4 | 1.2 | 5.2 | 2.8 |
| 27 | 6.9 | 3.2 | 8.1 | 1.5 |
| 28 | 6.9 | 3.0 | 8.7 | 2.0 |
| 29 | 7.4 | 1.2 | 5.3 | 1.9 |

Examples 30-32 and Comparative Example 9

Adhesive Compositions Containing a Caseinate (PHOSCAL)

Example 21 (Resin B+4% PHOSCAL) and Examples 28-29 were used as the Liquid B component in ADPER PROMPT L-POP Self-Etch Adhesive product (3M Company) and the resulting compositions evaluated for adhesion to enamel (AE) according to the Test Method described herein and the results compared to those for the commercial ADPER Adhesive product (Comparative Example (CE) 9). (For the AE tests of these materials, liquid A and B were mixed in a well; the adhesive was brushed onto the tooth surface for 20 sec, gently air-dried for 10 sec; an then light-cured for 10 sec.) The data are provided in Table 9.

TABLE 9

| | Composition | | Droplets | Enamel Adhesion |
|---|---|---|---|---|
| Example | Liquid A | Liquid B | A:B | MPa (SD) |
| CE 9 | ADPER Product | ADPER Product | 1:1 | 11.9 (2.3) |
| 30 | ADPER Product | Example 21 | 1:1 | 10.1 (2.7) |
| 31 | ADPER Product | Example 28 | 1:1 | 9.7 (4.5) |
| 32 | ADPER Product | Example 29 | 1:1 | 11.3 (4.1) |

Examples 33-37

Tooth Coating Compositions Containing a Caseinate (PHOSCAL)

PHOSCAL was mixed at 1%, 2%, 4%, and 8% by weight into a solution of 50% VBP, 40% ethanol, and 10% DIW. After 7 months at ambient conditions, the 1%, 2%, and 4% samples showed sediment and separation, while the 8% composition (designated Example 33) remained homogeneous, gelatinous, and stable.

PHOSCAL was mixed at various concentrations into a solution containing different film-forming polymers. The various compositions and their appearance are provided in Table 10. All of these compositions formed a hard, translucent-to-cloudy coating when dried onto a glass slide.

TABLE 10

Coating Compositions Containing PHOSCAL (Ingredients in Weight %)

| Ex. | Polymer | PHOSCAL | $Na_2FPO_3$ | DIW | EtOH | Appearance |
|---|---|---|---|---|---|---|
| 34 | AC-315 - 22.5 | 9 | 16 | 0 | 52.5 | Dispersible sediment |
| 35 | 940NF - 1.5 | 10 | 5 | 83.5 | 0 | Cloudy, homogeneous, stable gel |
| 36 | UR-450 - 90 | 1.2 | 0 | 8.8 | 0 | Opaque, homogeneous, stable |
| 37 | UR-450 - 65.6 | 2.4 | 0 | 18 | 14 | Opaque, homogeneous, stable |

Examples 38-44

Methacrylate Resin Compositions Containing a Caseinate (PHOSCAL)

Methacrylate light-curable resin compositions containing PHOSCAL (Examples 38-44) were prepared by combining the ingredients shown in Table 11. The paste compositions were evaluated for compressive strength, diametral tensile strength, spectral opacity, and adhesion to dentin (AD) and enamel (AE) according to the Test Methods described herein and the results are provided in Table 11. (For the AD and AE tests of these materials, a thin layer of the material was applied and allowed to sit for 30 sec before light-curing for 30 sec.)

TABLE 11

| Example | Composition (Numbers are Weight %) | Spectral Opacity | CS MPa (SD) | DTS MPa (SD) | Dentin Adhesion MPa (SD) | Enamel Adhesion MPa (SD) |
|---|---|---|---|---|---|---|
| 38 | PHOSCAL - 4 Resin C - 50 Filler B - 45 | 54.4 | 273 (14) | 53.7 (2.3) | 0.00 (0.00) | 8.1 (0.8) |
| 39 | PHOSCAL - 10 Resin E - 40 Filler C - 15 Filler D - 35 | 66.5 | 192 (36) | 39.6 (4.7) | NT | 3.0 (1.1) |
| 40 | PHOSCAL - 10 F2000 Resin - 40 Filler C - 15 Filler D - 35 | 60.5 | 215 (39) | 27.6 (14.2) | NT | 3.5 (0.96) |

TABLE 11-continued

| Example | Composition (Numbers are Weight %) | Spectral Opacity | CS MPa (SD) | DTS MPa (SD) | Dentin Adhesion MPa (SD) | Enamel Adhesion MPa (SD) |
|---|---|---|---|---|---|---|
| 41 | PHOSCAL - 8<br>Resin C - 42<br>Filler C - 15<br>Filler D - 35 | 56.4 | 169 (24) | 34.6 (8.8) | 10.6 (3.4) | 12.0 (2.4) |
| 42 | PHOSCAL - 8<br>Resin D - 42<br>Filler C - 15<br>Filler D - 35 | 51.5 | 183 (49) | 27.7 (9.1) | 3.0 (1.3) | 17.5 (5.7) |
| 43 | ResinD - 45<br>Filler C - 15<br>Example 1B - 40 | 45.7 | 180 (52) | 28.3 (8.7) | NT | NT |
| 44 | Resin D - 38<br>Filler C - 15<br>Filler D - 35<br>Example 2C - 12 | 50.3 | 186 (13) | 21.7 (3.3) | NT | NT |

Example 45 and Comparative Example 10

Self-Adhesive Composition Containing a Caseinate (PHOSCAL)

PHOSCAL (5% by weight; 0.03625 g) was added to the powder component of RelyX Unicem Cement in a MAXI-CAP capsule (3M Company) and then mixed in a ROTOMIX mixer for 10 seconds to afford a paste that was designated Example 45. Example 45 was evaluated for compressive and diametral tensile strengths according to the Test Methods described herein and the results compared to those for the commercial RelyX Unicem Maxicap Self-Adhesive Universal Resin Cement product (Comparative Example (CE) 10). The data are provided in Table 12 and show that the physical properties of the PHOSCAL-containing cement composition were basically the same as for the commercial RelyX Unicem cement.

TABLE 12

| Example | Composition | Compressive Strength MPa (SD) | Diametral Tensile Strength MPa (SD) |
|---|---|---|---|
| 45 | RelyX Unicem + PHOSCAL (5%) | 197 (32) | 52.3 (3.5) |
| CE 10 | RelyX Unicem | 199 (20) | 51.8 (13.9) |

Example 46 and Comparative Example 11

Paste-Paste RMGI System Containing a Caseinate (PHOSCAL)

PHOSCAL was added to the Paste B component of a Paste A/Paste B RMGI System and compared to the corresponding RMGI System without added PHOSCAL. The compositions of Paste A and the two Paste B components are shown in Tables 13A and 13B.

TABLE 13A

| Paste A Composition | |
|---|---|
| Ingredient | Concentration (Weight %) |
| HEMA | 2.05 |
| PEGDMA-400 | 7.35 |
| bisGMA | 2.56 |
| CPQ | 0.1 |
| EDMAB | 0.11 |
| Filler G | 16.7 |
| Filler E | 41.01 |
| Filler F | 30.12 |
| TOTAL: | 100 |

TABLE 13B

| | Paste B Compositions | |
|---|---|---|
| | Concentration (Weight %) | |
| Ingredient | Paste B1 | Paste B2 |
| DIW | 13.68 | 13 |
| PHOSCAL | 0 | 2.11 |
| HEMA | 5.35 | 5.09 |
| BHT | 0.02 | 0.02 |
| VBP | 24.87 | 23.67 |
| DPIHFP | 0.14 | 0.13 |
| Filler H | 28 | 28 |
| Filler D | 28 | 28 |
| TOTAL: | 100 | 100 |

Paste A was combined with Paste B1 (Comparative Example 11) and Paste A was combined with Paste B2 (Example 46; with PHOSCAL). The two blended pastes were evaluated for visual opacity (Macbeth values) and adhesion to dentin and enamel (without primer) according to the Test Methods described herein and results are provided in Table 13C.

TABLE 13C

| | Test Results | |
|---|---|---|
| Test | CE 11 | Example 46 |
| Visual Opacity | 0.33 | 0.32 |
| Dentin Adhesion (MPa) | 5.4 | 5.1 |
| Enamel Adhesion (MPa) | 2.6 | 5.6 |

Calcium and Phosphorus Ion Release Evaluations

Examples 6, 9-12, 17-19, 23-25, and 40 were evaluated for calcium and phosphorus release over time according to the Test Method described herein. Results are reported for the ICP method (calcium and phosphorus ions via inductively coupled plasma spectroscopy) and for the calcium-selective electrode (Ca-E) method (calcium ions only) and are provided in Table 14.

TABLE 14

Release of Calcium and Phosphorus Ions over Time
All Values in Units of Microgram (Ion)/g (Disk)/day

| | Day 7 | | | Day 30 | | | Day 60 | | | Day 180 | | |
|---|---|---|---|---|---|---|---|---|---|---|---|---|
| | ICP | | Ca-E | ICP | | Ca-E | ICP | | Ca-E | ICP | | Ca-E |
| Ex. | Ca | P | Ca | Ca | P | Ca | Ca | P | Ca | Ca | P | Ca |
| 6 | NT | NT | 3.17 | NT | NT | 3.56 | NT | NT | 3.72 | NT | NT | 0.91 |
| 9 | NT | NT | 2.66 | NT | NT | 2.76 | NT | NT | 3.79 | NT | NT | 6.33 |
| 10 | NT | NT | 1.87 | NT | NT | 2.72 | NT | NT | 3.92 | NT | NT | 3.17 |
| 11 | NT | NT | 2.30 | NT | NT | 3.16 | NT | NT | 3.33 | NT | NT | 3.30 |
| 12 | NT | NT | 2.26 | NT | NT | 2.01 | NT | NT | 2.44 | NT | NT | 2.95 |
| 17 | 178.1 | 301.7 | NT | 17.12 | 29.24 | NT | NT | NT | 6.89 | NT | NT | 0.48 |
| 18 | NT | NT | 19.17 | NT | NT | 4.58 | NT | NT | 1.94 | NT | NT | 1.45 |
| 19 | NT | NT | NT | 12.65 | 43.05 | NT | NT | NT | 2.02 | NT | NT | 0.21 |
| 23 | NT | NT | 1.96 | NT | NT | 2.69 | NT | NT | 3.13 | NT | NT | NT |
| 24 | NT | NT | 2.08 | NT | NT | 2.38 | NT | NT | 3.22 | NT | NT | 1.26 |
| 25 | NT | NT | 1.53 | NT | NT | 3.79 | NT | NT | 3.48 | NT | NT | NT |
| 40 | NT | NT | 2.62 | NT | NT | 0.81 | NT | NT | 0.79 | NT | NT | NT |

Dentin Remineralization Evaluations

Examples 4 (Vitrebond Powder treated with 5% PHOS-CAL) and Example 24 were evaluated for dentin remineralization according to the Test Method described herein and showed remineralization after 3 weeks adjacent to and underneath the applied material in the area of the exposed lesion.

Enamel Remineralization Evaluations

Example 41 was evaluated for enamel remineralization according to the Test Method described herein. After 3 weeks storage in an artificial saliva solution, the samples were sliced and optical micrographs taken. In some images, new mineral formation was visible as bright white regions under the material within the lesion. New mineral formation was not seen in the areas exposed to the artificial saliva.

Resistance to Demineralization in Dentin Evaluations

Example 4A (Vitrebond Powder treated with 1% PHOS-CAL), Example 10 (RMGI composition containing PHOS-CAL) and comparative Examples 1 and 5 (VITREBOND Light Cure Glass Ionomer Liner/Base and FILTEK Z250 Universal Restorative System, respectively) were evaluated for resistance to demineralization in dentin according to the Test Method described herein. The resulting microradiographs and associated data (Table 15) showed that the VITREBOND product enhanced resistance to acid attack versus FILTEK Z250 and that Examples 4A and 10 enhanced this resistance dramatically.

TABLE 15

Percent of Samples in Each Lesion Category

| Lesion Category | VITREBOND | Z250 | Ex. 4A | Ex. 10 |
|---|---|---|---|---|
| Full Lesion | 27.3 | 100.0 | 8.3 | 10.5 |
| Lesion thinner near material | 33.3 | 0.0 | 25.0 | 31.6 |
| Intact dentin near material, lesion farther away | 39.4 | 0.0 | 66.7 | 57.9 |
| No lesion discernible | 0.0 | 0.0 | 0.0 | 0.0 |

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A dental filler comprising a treated surface, wherein the treated surface comprises a caseinate, wherein the treated surface further comprises a silane.

2. The dental filler of claim 1, wherein the caseinate comprises a salt of calcium, phosphate, fluoride, or combinations thereof.

3. The dental filler of claim 1 wherein the treated surface is amorphous.

4. The dental filler of claim 1 wherein the treated surface is at least partially crystalline.

5. The dental filler of claim 1, wherein the porous dental filler is selected from the group consisting of porous particles, porous agglomerates of particles, and combinations thereof.

6. The dental filler of claim 1, wherein the dental filler comprises nanoparticles, agglomerates of nanoparticles, or combinations thereof.

7. The dental filler of claim 1, wherein the dental filler comprises metal oxides, metal fluorides, metal oxyfluorides, or combinations thereof.

8. The dental filler of claim 7, wherein the metal is selected from the group consisting of heavy metals, non-heavy metals, and combinations thereof.

9. The dental filler of claim 1, wherein the dental filler is an oxide, a fluoride, or an oxyfluoride of an element selected from the group consisting of Groups 2-5 elements, Groups 12-15 elements, Lanthanide elements, and combinations thereof.

10. The dental filler of claim 9, wherein the element is selected from the group consisting of Ca, Sr, Ba, Y, La, Ce, Pr, Nd, Pm, Sm, Eu, Gd, Tb, Dy, Ho, Er, Tm, Yb, Lu, Ti, Zr, Ta, Zn, B, Al, Si, Sn, P, and combinations thereof.

11. The dental filler of claim 1, wherein the dental filler comprises a glass, an amorphous material, or a crystalline material.

12. The dental filler of claim 1, wherein the dental filler comprises a source of fluoride ions.

13. The dental filler of claim 12, wherein the dental filler comprises a fluoroaluminosilicate glass.

14. The dental filler of claim 1, wherein the treated surface further comprises a source of fluoride ions.

15. The dental filler of claim 1, wherein the treated surface further comprises an antibacterial agent.

16. The dental filler of claim 1, wherein the treated surface further comprises Sr, Mg, Zn, Sn, Ag, or combinations thereof.

17. A method of making a dental filler comprising a treated surface, the method comprising treating the surface of the dental filler with a caseinate, wherein the treated surface further comprises a silane.

18. The method of claim 17 wherein the caseinate comprises a salt of calcium, phosphate, fluoride, or combinations thereof.

19. The method of claim 17, wherein treating is selected from the group consisting of coating, infiltrating, and combinations thereof.

20. The method of claim 17, wherein treating comprises:
dissolving, dispersing, or suspending the caseinate in a liquid;
combining the liquid with the dental filler; and
removing at least a portion of the liquid to provide the treated surface.

21. The method of claim 20 wherein the liquid is non-aqueous.

22. The method of claim 20 wherein the liquid comprises water.

23. The method of claim 17, wherein the porous dental filler is selected from the group consisting of porous particles, porous agglomerates of particles, and combinations thereof.

24. The method of claim 17, wherein the dental filler comprises nanoparticles, agglomerates of nanoparticles, or combinations thereof.

25. The method of claim 17, wherein the dental filler comprises metal oxides, metal fluorides, metal oxyfluorides, or combinations thereof.

26. The method of claim 25, wherein the metal is selected from the group consisting of heavy metals, non-heavy metals, and combinations thereof.

27. The method of claim 17, wherein the dental filler is an oxide, a fluoride, or an oxyfluoride of an element selected from the group consisting of Groups 2-5 elements, Groups 12-15 elements, Lanthanide elements, and combinations thereof.

28. The method of claim 27, wherein the element is selected from the group consisting of Ca, Sr, Ba, Y, La, Ce, Pr, Nd, Pm, Sm, Eu, Gd, Tb, Dy, Ho, Er, Tm, Yb, Lu, Ti, Zr, Ta, Zn, B, Al, Si, Sn, P, and combinations thereof.

29. The method of claim 17, wherein the dental filler comprises a glass, an amorphous material, or a crystalline material.

30. The method of claim 17, wherein the dental filler comprises a source of fluoride ions.

31. The method of claim 30, wherein the dental filler comprises a fluoroaluminosilicate glass.

32. The method of claim 17, wherein the treated surface further comprises a source of fluoride ions.

33. The method of claim 17, wherein the treated surface further comprises an antibacterial agent.

34. The method of claim 17, wherein the treated surface further comprises Sr, Mg, Zn, Sn, Ag, or combinations thereof.

35. A dental composition comprising a dental filler according to claim 1.

36. The dental composition of claim 35, wherein the caseinate comprises a salt of calcium, phosphate, fluoride, or combinations thereof.

37. The dental composition of claim 35 further comprising an additional filler.

38. The dental composition of claim 35 further comprising water.

39. The dental composition of claim 35 further comprising a water-dispersible, polymeric film former.

40. The dental composition of claim 35 further comprising a hardenable resin.

41. The dental composition of claim 40, wherein the hardenable resin comprises acid functionality.

42. The dental composition of claim 41, wherein the acid functionality comprises carboxylic acid functionality, phosphoric acid functionality, phosphonic acid functionality, sulfonic acid functionality, or combinations thereof.

43. The dental composition of claim 40 further comprising an initiator system.

44. The dental composition of claim 40, wherein the hardenable resin comprises an ethylenically unsaturated compound.

45. The dental composition of claim 44, wherein the ethylenically unsaturated compound is selected from the group consisting of an ethylenically unsaturated compound with acid functionality, an ethylenically unsaturated compound without acid functionality, and combinations thereof.

46. The dental composition of claim 35, wherein the composition is selected from the group consisting of dental primers, dental adhesives, cavity liners, cavity cleansing agents, cements, coatings, varnishes, orthodontic adhesives, restoratives, sealants, desensitizers, and combinations thereof.

47. A method of treating a tooth structure comprising contacting the tooth structure with a dental composition according to claim 35.

48. A method of remineralizing a tooth structure comprising placing a dental composition according to claim 36 in an oral environment.

49. A method of reducing sensitivity of a tooth structure comprising placing a dental composition according to claim 36 in an oral environment.

50. A method of protecting a tooth structure comprising placing a dental composition according to claim 36 in an oral environment.

51. A method of delivering ions to an oral environment comprising:
placing a dental composition according to claim 36 in the oral environment, wherein the ions comprise elements selected from the group consisting of calcium, phosphorus, fluorine, and combinations thereof.

52. A method of preparing a dental article comprising:
combining a dental filler according to claim 1 and a hardenable resin to form a dental composition; and
hardening the composition to fabricate a dental article selected from the group consisting of crowns, fillings, mill blanks, orthodontic devices, and prostheses.

53. A dental composition comprising:
a dental filler according to claim 1;
a hardenable resin; and
a water-dispersible, polymeric film former.

54. The dental composition of claim 53, wherein the hardenable resin and the water-dispersible, polymeric film former are the same.

55. The dental composition of claim 53, wherein the hardenable resin and the water-dispersible, polymeric film former are different.

56. The dental filler according to claim 1, wherein the dental filler is porous.

57. The method according to claim 17, wherein the dental filler is porous.

* * * * *

UNITED STATES PATENT AND TRADEMARK OFFICE
CERTIFICATE OF CORRECTION

PATENT NO. : 8,278,368 B2
APPLICATION NO. : 11/719472
DATED : October 2, 2012
INVENTOR(S) : Richard P Rusin It is certified that error appears in the above-identified patent and that said Letters Patent is hereby corrected as shown below:

First Page, Col. 1 (Assignee)
Lines 1-2, delete "3M Innovatve Properties Company, St. Pauk, MN (US)" and insert -- 3M Innovative Properties Company, St. Paul, MN (US) --

First Page, Col. 1
Please add -- Related U.S. Application Data [62] U.S. Application No. 10/989,523, filed on Nov. 16, 2004 --

Page 3, Col. 1 (Other Publications)
Line 39, delete "8 pages." and insert -- received June 9, 1998, 8 pages. --

Line 43, delete "8 pages." and insert -- received June 9, 1998, 8 pages. --

Page 3, Col. 2 (Other Publications)
Line 62, delete "8 pages." and insert -- received June 9, 1998, 8 pages. --

Line 65, delete "8 pages." and insert -- received June 9, 1998, 8 pages. --

Column 1
Line 10, delete "Nov. 16, 2007," and insert -- Nov. 16, 2004 --

Column 4
Line 48, delete "fillet" and insert -- filler --

Column 9
Line 7, delete "bis[β-(3" and insert -- bis[1-(3 --

Column 14
Line 62, delete ""macroiners"." and insert -- "macromers". --

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,278,368 B2

Column 18
Line 23, delete "$C+^2$" and insert -- $Ca+^2$ --

Column 26
Line 16 (approx.), delete "Resin B)" and insert -- (Resin B) --